United States Patent
Nguyen et al.

(10) Patent No.: US 10,499,857 B1
(45) Date of Patent: Dec. 10, 2019

(54) MEDICAL PROTOCOL CHANGE IN REAL-TIME IMAGING

(71) Applicant: DEEPRADIOLOGY, INC., Santa Monica, CA (US)

(72) Inventors: Kim Nguyen, Santa Monica, CA (US); Robert Burnham Lufkin, Santa Monica, CA (US); Jameson Tyler Merkow, San Diego, CA (US)

(73) Assignee: DEEPRADIOLOGY INC., Santa Monica, CA (US)

( * ) Notice: Subject to any disclaimer, the term of this patent is extended or adjusted under 35 U.S.C. 154(b) by 0 days.

(21) Appl. No.: 15/709,293

(22) Filed: Sep. 19, 2017

(51) Int. Cl.
*A61B 5/00* (2006.01)
*G06N 3/08* (2006.01)
*G06T 7/00* (2017.01)

(52) U.S. Cl.
CPC ............. *A61B 5/7267* (2013.01); *G06N 3/08* (2013.01); *G06T 7/0012* (2013.01); *G06T 2207/20081* (2013.01); *G06T 2207/30004* (2013.01)

(58) Field of Classification Search
CPC ............. G06T 7/30004; G06T 7/30008; G06T 7/10072; G06T 7/10081; G06T 7/10104; G06T 7/10108; G06T 7/10112; G06T 7/20112; G06T 7/20212; G06T 7/0012; G06T 2207/20081; G06T 2207/30004; G06T 7/0081; A61B 5/7267; G06N 3/08
See application file for complete search history.

(56) References Cited

U.S. PATENT DOCUMENTS

| | | | | |
|---|---|---|---|---|
| 5,157,733 A * | 10/1992 | Takeo | ............... | G06T 7/00 128/925 |
| 5,790,690 A * | 8/1998 | Doi | ............... | G06T 7/0012 382/128 |
| 5,873,824 A * | 2/1999 | Doi | ............... | G06K 9/00 128/925 |
| 8,798,345 B2 * | 8/2014 | Sasaki | ............... | G06T 7/0012 382/128 |
| 9,589,374 B1 * | 3/2017 | Gao | ............... | G06T 11/008 |
| 10,249,042 B2 * | 4/2019 | Jung | ............... | G16H 40/63 |
| 2005/0049497 A1 * | 3/2005 | Krishnan | ............... | G06F 19/321 600/437 |
| 2005/0283365 A1 | 12/2005 | Mizutani et al. | | |
| 2006/0136259 A1 | 6/2006 | Weiner et al. | | |

(Continued)

OTHER PUBLICATIONS

Alexander J.T. "Practice Policy and Quality Initiatives: Decreasing Variability in Turnaround Time for Radiographic Studies from the Emergency Department" *RadioGraphics* Mar. 2013 vol. 33: 361-371, 10.1148/rg.332125738.

(Continued)

*Primary Examiner* — Wesley J Tucker
(74) *Attorney, Agent, or Firm* — Steinfl + Bruno LLP

(57) ABSTRACT

Methods and systems for medical diagnosis by machine learning are disclosed. Imaging data obtained from different medical techniques can be used as a training set for a machine learning method, to allow diagnosis of medical conditions in a faster a more efficient manner. A three-dimensional convolutional neural network can be employed to interpret volumetric data available from multiple scans of a patient. The imaging data can be analyzed in real-time to prescribe additional testing while the patient is still within the medical facility.

20 Claims, 13 Drawing Sheets

(56) References Cited

U.S. PATENT DOCUMENTS

| | | | |
|---|---|---|---|
| 2008/0240532 A1* | 10/2008 | Carneiro | G06K 9/3233 382/131 |
| 2012/0330876 A1 | 12/2012 | Bryce | |
| 2013/0121548 A1 | 5/2013 | Kovalan et al. | |
| 2014/0185900 A1* | 7/2014 | Lee | G06T 7/0014 382/131 |
| 2016/0174902 A1* | 6/2016 | Georgescu | G06T 7/73 600/408 |
| 2017/0024887 A1 | 1/2017 | Biegert et al. | |
| 2017/0046616 A1 | 2/2017 | Socher et al. | |
| 2017/0091528 A1 | 3/2017 | Savvides et al. | |
| 2017/0098140 A1 | 4/2017 | Wang et al. | |
| 2017/0140240 A1 | 5/2017 | Socher | |
| 2017/0287134 A1* | 10/2017 | Abedini | G06K 9/622 |
| 2017/0294014 A1* | 10/2017 | Nakano | G06T 7/0012 |
| 2018/0061058 A1 | 3/2018 | Xu et al. | |
| 2018/0129911 A1* | 5/2018 | Madabhushi | G06K 9/4628 |
| 2018/0174051 A1 | 6/2018 | Knittel | |
| 2018/0225820 A1 | 8/2018 | Liang et al. | |
| 2018/0232603 A1* | 8/2018 | Shim | A61B 6/00 |
| 2018/0232883 A1 | 8/2018 | Sethi et al. | |
| 2018/0247416 A1 | 8/2018 | Ruda et al. | |
| 2019/0073569 A1 | 3/2019 | Ben-Ari et al. | |
| 2019/0159744 A1* | 5/2019 | Mensah | A61B 6/5217 |
| 2019/0164278 A1* | 5/2019 | Abramoff | G06T 7/75 |
| 2019/0164642 A1* | 5/2019 | Hartung | G16H 30/20 |

OTHER PUBLICATIONS

Bershad E.M. et al., "Multidisciplinary protocol for rapid head computed tomography turnaround time in acute stroke patients" *J Stroke Cerebrovasc Dis* Jun. 2015; 24(6):1256-1261.
Brady A. et al., "Discrepancy and Error in Radiology: Concepts, Causes and Consequences" *The Ulster Medical Journal*2012; 82(1):3-9.
Final Office Action for U.S. Appl. No. 15/707,918, filed Sep. 18, 2017 on behalf of Deep Radiology Inc. dated Jul. 3, 2019 15 pages.
Girshick R et al. "Fast R-CNN" *International Conference on Computer Vision*2015.
Girshick R. et al., "Rich feature hierarchies for accurate object detection and semantic segmentation" *Computer Vision and Pattern Recognition*2014.
Gunn A.J. "Toward improved radiology reporting practices in the emergency department: a survey of emergency department physicians".*J Radiol Radiat Ther*2013 1(2):2013.
He K. et al., "Deep Residual Learning for Image Recognition" *arXiv.org vol. cs.CV*. Dec. 10, 2015.
Hinton G. et al., "Distilling the knowledge in a neural network" *arXiv preprint arXiv*:1503.025322015.
Honari et al., "Recombinator Networks: Learning Coarse-to-Fine Feature Aggregation" arXiv.org vol. cs.Cv. Nov. 23, 2015.
Ioffe et al., "Batch normalization: Accelerating deep network training by reducing internal covariate shift." arXiv preprint arXiv:1502.03167, 2015.
Kirillov a. et al., "Joint Training of Generic CNN-CRF Models with Stochastic Optimization" *arXiv*:1511.05067v3 [cs. CV] Sep. 14, 2016.
Krizhevsky a. et al., "Imagenet classification with deep convolutional neural networks" *Advances in Neural Information Processing System*1097-1105,2012.
Lai M. "Deep Learning for Medical Image Segmentation" arXiv.org vol. cs. LG May 8, 2015.
Lee et al., "Deeply-supervised nets" *AISTATS*2015.

Lee K. et al., "Recursive Training of 2D-3D Convolutional Networks for Neuronal Boundary Prediction" Advances in Neural Information Processing Systemspp. 3559-3567 2015.
Lenc K. et al., "Understanding image representations by measuring their equivariance and equivalence" arXiv preprint arXiv:1411.5908, 2014.
Mahendran a et al., "Understanding deep image representations by inverting them" arXiv preprint arXiv:1412.0035, 2014.
Merkow et al., "Structural Edge Detection for Cardiovascular Modeling" *Medical Image Computing and Computer-Assisted Intervention*-MICCAI 2015. Springer,2015 735-742.
Merkow J. et al., "Dense Volume-to-Volume Vascular Boundary Detection" *International Conference on Medical Image Computing and Computer-Assisted Intervention* 2016.
Non-Final Office Action for U.S. Appl. No. 15/707,918, filed Sep. 18, 2017, on behalf of Deepradiology Inc. dated Nov. 30, 2018. 16 pages.
Non-Final Office Action for U.S. Appl. No. 15/709,223, filed Sep. 19, 2017, on behalf of Deepradiology, Inc. dated Sep. 18, 2018. 8 pgs.
Non-Final Office Action for U.S. Appl. No. 15/711,541, filed Sep. 21, 2017 on behalf of Deepradiology, Inc. dated Mar. 4, 2019. 16 pages.
Non-Final Office Action for U.S. Appl. No. 15/707,942, filed Sep. 18, 2017 on behalf of Deep Radiology Inc. dated Jun. 26, 2019 13 pages.
Notice of Allowance for U.S. Appl. No. 15/709,223, filed Sep. 19, 2017 on behalf of Deep Radiology Inc dated Jul. 1, 2019 8 pages.
Pinto A. et al., "Spectrum of diagnostic errors in radiology" *World of Journal of Radiology*2010,2(10):377-383.
Ren S. et al., "Faster R-CNN: Towards real-time object detection with region proposal networks" *Advances in Neural Information Processing Systems*2015.
Restriction Requirement for U.S. Appl. No. 15/398,635, filed Jan. 4, 2017, on behalf of Deepradiology, Inc. dated Dec. 11, 2018.5 pages.
Restriction Requirement for U.S. Appl. No. 15/712,030, filed Sep. 21, 2017 on behalf of Deepradiology Inc. dated Feb. 28, 2019. 5 pages.
Roth H.R. et al., "DeepOrgan: Multi-level Deep Convolutional Networks for Automated Pancreas Segmentation" arXiv.org2015.
Rumelhart D.E. et al., "Learning representations by back-propagating errors" Naturevol. 323, p. 533-536,1986.
Rumelhart et al "Learning internal representations by error propagation, Parallel distributed processing: explorations in the microstructure of cognition" vol. 1 pp. 318362, MIT Press Cambridge, MA, USA,1986.
Saver J.L. "Time to treatment with intravenous tissue plasminogen activator and outcome from acute ischemic stroke" *JAMA* Jun. 2013; 309 (23): 2480-2488.
Shen W. et al., "Multi-scale Convolutional Neural Networks for Lung Nodule Classification" IPMI2015.
Sun M. et al., "Multiple Instance Learning Convolutional Neural Networks for Object Recognition"arXiv.org Oct. 2016.
Szegedy C. et al., "Going deeper with convolutions" Proceedings of the IEEE Conference on Computer Vision and Pattern Recognition2015.
Tran et al "Deep End2End Voxel2Voxel Prediction" arXiv.org vol. cs.Cv. Nov. 20, 2015.
Wang et al., "Training Deeper Convolutional Networks with Deep Supervision" ArXiv 1505.02496 May 11, 2015.
Wong W. et al., "Outsourced teleradiology imaging services: an analysis of discordant interpretation in 124,870 cases"J Am Coll Radiol. Jun. 2005; 2(6): 478-484.
Zheng Y. et al., "3D Deep Learning for Efficient and Robust Landmark Detection in Volumetric Data" *SpringerLink* Nov. 2015.

* cited by examiner

MEDICAL PROTOCOL CHANGE IN REAL-TIME IMAGING

CROSS REFERENCE TO RELATED APPLICATIONS

The present application may be related to U.S. patent application Ser. No. 15/398,635, filed on Jan. 4, 2017, the disclosure of which is incorporated herein by reference in its entirety.

TECHNICAL FIELD

The present disclosure relates to medical diagnosis. More particularly, it relates to medical protocol change in real-time imaging.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

SUMMARY

Figure 1:
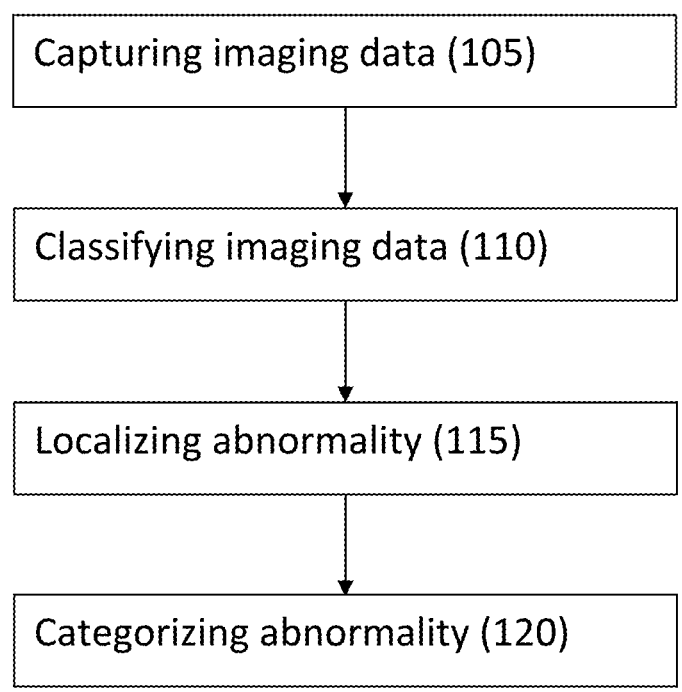
FIG. 1 illustrates an overview of one embodiment of a diagnosing process of the present disclosure.

In a first aspect of the disclosure, a device is described, the device comprising: a processor and memory configured to implement the steps of: receiving imaging data relating to a body part of a human patient; classifying by machine learning the imaging data into a normal or an abnormal class and categorizing the abnormalities; and if the imaging data is classified as abnormal, prescribing collection of additional imaging data of the body part while the human patient is still present at the medical imaging facility.

In a second aspect of the disclosure, a method is described, the method comprising receiving, by a computer, imaging data relating to a body part of a human patient; classifying by machine learning the imaging data into a normal or an abnormal class; and if the imaging data is classified as abnormal, prescribing collection of additional imaging data of the body part while the human patient is still present at the medical imaging facility.

DETAILED DESCRIPTION

The present disclosure relates to the automatic or assisted analysis of medical imaging data for the purpose of diagnosis of abnormalities, in a real-time setting. Specifically, the present disclosure describes the use of automatic data analysis with machine learning methods, to increase the efficacy of medical imaging.

For example, a patient may be required to undergo some type of medical test, such as a computed tomography (CT) or other radiology tests such as simple X-ray scans. Typically, the patient can either be subject to an extensive set of scans, or a limited set of scans. If the set of scans is too broad, for example encompassing a broad part of the body, the patient may be required, at a later time, to return to the testing center for a more detailed scan of a sub-region of that part of the body. For example, a medical doctor typically analyzes the scans at a later stage, with the scans being taken by a lab technician. If the doctor identifies a possible anomaly, the doctor may requests a more detailed set of scans in a specific part of the body, or the same scan for the entire part of the body, but taken with some kind of enhancement such as a liquid contrast. In these cases, the patient has to return to the medical facility, increasing patient discomfort, costs, and time requirement.

Alternatively, the doctor may request a higher number of scans, or a more extensive set of scans from the outset. However, this may increase unnecessarily the amount of scans which the patients is subjected to. For example, the amount of radiation absorbed by the patient may be unnecessarily increased, with possible adverse medical effects on the patient.

Therefore, it would be helpful to have a way to analyze the data in real-time, during a medical test, and provide immediate recommendations to the lab technician on whether further scan or testing is required. An automated algorithm capable of analyzing medical imaging data and provide a diagnosis recommending further scans would therefore be advantageous. Such an automated algorithm could direct the technician to possible problematic areas, providing an opportunity to scan these areas before the patient has left the medical facility.

Exemplary methods, based on machine learning, capable of analyzing medical data have been described in U.S. patent application Ser. No. 15/398,635, the disclosure of which is incorporated by reference in its entirety. The present disclosure describes how these methods can be modified to perform real-time analysis and recommendations with regard to medical tests such as, for example, CT scans, X-rays, biological tissue staining, and other types of medical tests.

The analysis carried out by the machine learning algorithms described herein is ordinarily performed by physicians trained in the field of Radiology, Cardiology, Dermatology and Pathology. In the present disclosure, "assisted analysis" refers to any collection of methods and systems that assist the medical professional to arrive at a diagnosis, without replacing the human expert. In the present disclosure, "automated analysis" refers to any collection of methods and systems that replace the medical professional by providing a diagnosis directly to the patient.

Analysis of medical imaging data is often one of the first steps in the diagnosis and determination of course of treatment. For urgent or emergency care, it is paramount that such analysis be performed in a timely manner. For instance, the stroke protocol requires emergency room (ER) patients to undergo a computed tomographic study of the head, the result of which is critical to determine the course of treatment, where certain treatment options are only available for a few hours, see Ref. [13]. In such circumstances, the time spent by the radiologist to analyze the imaging, estimated on average at around 30 minutes (see Refs. [14,17]), becomes a critical bottleneck. Assisted or automated analysis can help reduce the time necessary to arrive at a diagnosis.

In addition, human error during routine diagnosis is often unavoidable even for highly trained medical professionals, for example due to time constraints set by financial reasons. Nevertheless, such errors drive the cost of medical insurance, which has an adverse effect on the healthcare system at large. Assisted or automated analysis can help reduce the error in diagnosis, currently estimated at least as 1-5% (see Refs. [19,20]).

Both time to diagnosis and errors in the diagnosis could decrease by increasing the number of trained physicians available to perform second readings. This would cause a significant increase in the cost of healthcare, however. On the contrary, assisted or automated analysis can help reduce the cost of diagnosis, thus making high-quality medical care possible in situations where no highly trained physicians are available, or where the cost of their services would be prohibitive.

Assisted or automated analysis of medical imaging could therefore help reduce the time, error, and cost associated with diagnosis by a trained physician. The latter is partly due to the fact that training is costly and time consuming, requiring each physician to undergo years of preparation. The use of machine learning techniques allows the benefits of training and experience to be shared globally by all systems, rather than each individual system being trained in isolation. It also allows "global lifelong learning" whereby each error made by any one system can serve to improve the performance of all systems.

Nomenclature

Medical imaging data includes, but is not limited to, anatomical imaging such as X-ray slides, computerized tomography (CT), magnetic-resonance (MR), as well as functional data such as diffusion-tensor (DT), functional MR, and gene-expression data. It also includes optical imaging of tissue slices, for the determination of various pathologies. An imaging study comprises a collection of imaging data captured from the same subject during the same session, for instance a collection of two-dimensional (2D) slices comprising a volume image in CT or MR, or a collection of images captured during an ultrasound examination. As visible in FIG. 1, imaging data is captured or provided before analysis (105).

Analysis consists of, at least, the binary classification of each imaging study into two classes, normal or abnormal. This task can be referred to as classification (110). In addition, in the case of a positive (abnormal) study, suitable analysis typically provides indication of where in the imaging study (e.g. which slide, which locations within the slide) the abnormality is present. This task is sometimes referred to as detection, or as localization (115), which could be limited to a location or a coarse region of an image, like a quadrant or a bounding box, or the fine delineation of the region where the pathology is manifested (segmentation). Finally, a complete diagnosis requires the categorization (120) of the pathology, to determine the nature and severity of the abnormality. This step is carried out by classifying the abnormality as one of a number of abnormalities recognized by medical professional protocols.

The present disclosure pertains to the exploitation of machine learning techniques for the development of assisted or automated analysis of medical imaging data. Machine Learning (ML) refers generically to the design of classifiers or regressors and the associated algorithm and computational systems, without knowledge of the underlying distribution other than for the availability of samples from said distribution. Such samples are commonly referred to as a training set.

Exemplary Applications

The present application can be applied with reference to difference imaging protocols. An imaging protocol specifies the parameters for image acquisition during a medical imaging scan. Imaging protocols used in any number of medical imaging techniques comprise, for example, radiology, e.g. CT, magnetic resonance, ultrasound, computed radiology (CR), nuclear medicine imaging (MN), mammography; pathology, e.g. histology, cytology, electron microscopy (EM); cardiology, dermatology, and ophthalmology.

For example, the imaging protocol for a CT head scan may specify a set of parameters for the scan, such as field of view, slice thickness, and scan plane orientation, e.g. axial, sagittal, coronal, or oblique. Different imaging protocols may be used for optimally scanning the patient depending on the pathology in a given medical imaging examination. Unfortunately, though, the presence of pathology is often not known when the scanning is being performed and is usually not available until the study is interpreted.

Current availability of radiologists does not allow for interpretation of medical images in most cases at the time of scanning the patient. As a consequence of the exact pathology being unknown at the time of scanning, the imaging protocols are not optimized for any given pathology. As mentioned above in the present disclosure, the resulting scanning protocols tend to err between two extremes of coverage, as in the following.

In some cases, the imaging protocols obtain the very minimum coverage to detect any abnormality. This method has the limitation that the patient can be recalled for a second examination for specialized sequences as required by different pathologies.

In other cases, the imaging protocols obtain maximum coverage on all patients for all possible contingent pathologies. This method has the limitation that all patients can receive unnecessary extra scans/radiation and the process will consume more time.

The methods described in the present disclosure allow the pathology to be detected at the time of scanning by artificial intelligence (AI). As a consequence, any additional sequences can be obtained at the time of scanning. These methods result in customized scanning protocols that are optimized for all patients based on the pathology that the scans contain.

Automated or assisted analysis in real-time can therefore decrease the amount of scans performed, as well as the radiation exposure, for the patient, as well as decreasing the amount of scanning recalls for the patient. In the following, an exemplary embodiment is described with reference to the exemplary technique of a CT scan of the head, however similar embodiments may be carried out for a variety of different medical tests.

For the exemplary technique of a CT scan of the head, the minimum coverage scanning is performed to allow diagnosis. For example, axial thick sections are taken through the head. In this context, the sections are termed thick as they cover a larger region of the head, while thin sections would cover the same region in more details. The AI is then run on the scans and if no abnormality is detected, the study is completed and the patient can be sent home.

If a pathology is detected by the AI which requires additional scanning, the additional scanning can be performed immediately, thanks to the real-time feedback given by the AI to the laboratory technician. For example, thin sections are taken of the same region previously scanned, or of a sub-region where the possible abnormality is located. These thin sections allow a higher resolution scanning compared to the thick sections of the initial scan. Subsequently, the patient can be sent home.

In the example above, the optimum individualized imaging scan protocol is created for each patient using the AI, greatly decreasing any need for recall examinations or unnecessary scanning sequences.

As known to the person of ordinary skill in the art, automatic optimization of X-ray scanning protocols to adjust X-ray dosage based on the size of the patient are currently in use. The present disclosure, however, introduces a different methodology based on deep learning and artificial intelligence to infer diagnostic information. This type of automated scanning analyzes the content of the images rather than performing a simple single measurement such as patient size. 'Patient size' refers to a measurement of the size of the patient with respect to the radiation dose to be administered, e.g. larger patients receive a higher exposure for the same level of image quality. The present disclosure describes a more sophisticated analysis and customization of the protocols compared to what was previously possible.

In the embodiment described above, discussing a CT scan of the head, the technologist initially performs a basic CT scan of the head on the patient. When the initial scan is completed the patient will typically be still on the table. The scan data is sent to a machine learning neural network, for example a deep learning AI system utilizing several deep convolutional neural networks. The output of the AI system is categorized as either normal or not normal. In several embodiments, the system processes the initial CT scan results in real-time. For example, the system can process the scan in less than 120 seconds. The scan result can be returned to the information technologist or laboratory technician in the CT scanner location, with the patient. If the AI indicates a normal study the technologist concludes the scanning and sends the patient home. If the AI indicates an abnormal study the technologist can obtain additional views from the CT scanner, to provide more detailed images of the brain for later analysis and interpretation, either by the AI, a human doctor, or both.

Figure 5:
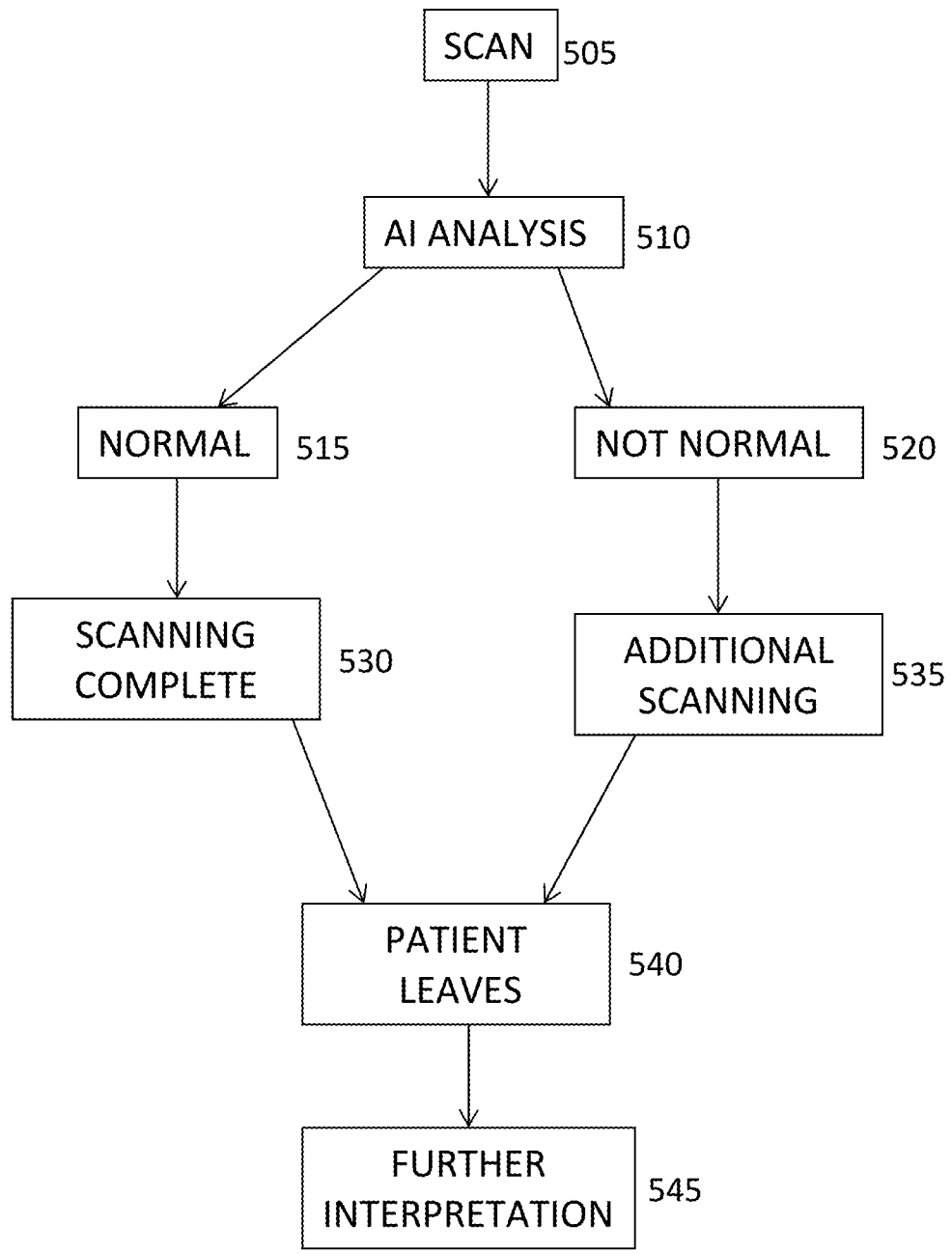
FIGS. 5-7 illustrate embodiments of the real-time protocols of the present disclosure.

FIG. 5 illustrates an exemplary embodiment of the present disclosure. An initial scan (505), is sent to AI processing and interpretation (510), which categorizes the scan as normal (515) or abnormal (520). In the first case (530) the scan is complete and the patient can be sent home (540). In the second case (535), additional scanning is prescribed by the AI according to the specific potential abnormality detected in the initial scan. The scan, either the initial scan or the augmented scan, is then sent for further interpretation to either a human doctor, an AI, or both (545).

Figure 6:
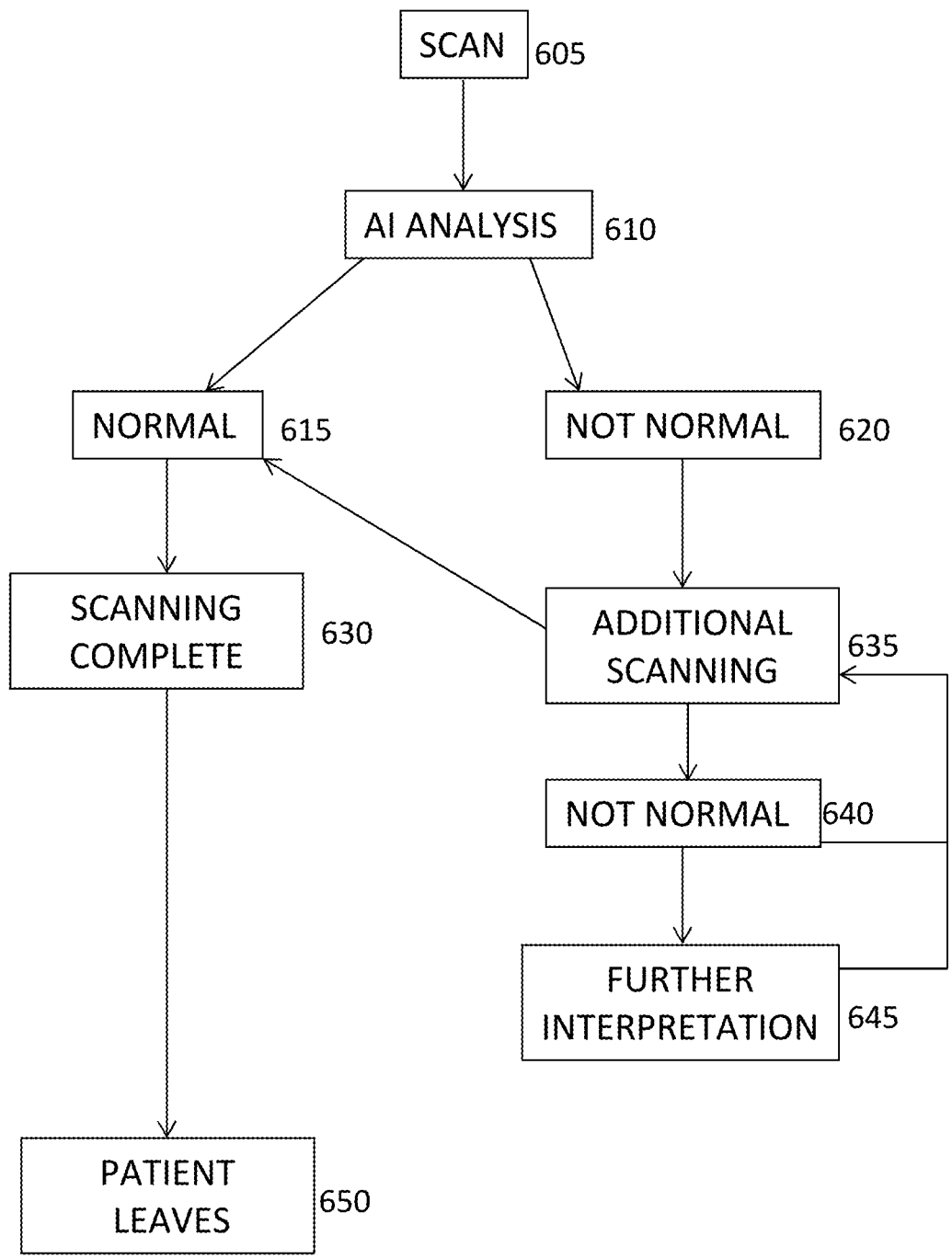

In some embodiments, the step (545) can be carried out by the AI in real-time. For example, the AI may recommend additional scans while the patient is still at the medical facility. Therefore, the method can be modified to carry out step (540) at a later time. For example, FIG. 6 illustrates an embodiment with additional AI processing and scans in real-time. The initial scan may be, for example, a CT scan, or a tissue staining.

As illustrated in FIG. 6, a scan (605) is performed, followed by an initial AI analysis (610). At any time, if the scan returns a normal result (615), the scan is complete (630) and the patient is sent home (650). If the AI returns an abnormal category (620), additional scanning is recommended (635), followed by additional loops (640) and further AI interpretation (645).

For example, the initial scan may indicate a possible pituitary mass. The AI will return an abnormal result and recommend a rescan with direct coronal images. The AI may recommend different courses of action depending on the specific abnormality. For example, the AI may request different views of the scanned area, or request a rescan with a contrast. For example, if the direct coronal images confirm a definite pituitary mass, the AI may recommend a rescan with contrast. The AI may then determine if the pituitary mass is enhanced. As known to the person of ordinary skill in the art, an enhanced mass may be detected due to enhanced vascularity indicated by the scan with contrast. The enhanced vascularity may be caused by the specific pathology causing the pituitary mass. In some embodiments, the AI may recommend the immediate supervision of a human doctor, for reviewing of the abnormality. The human doctor may also, in appropriate cases, recommend an immediate admission to the emergency department of a hospital.

In other embodiments, the methods described above can also be applied to other types of medical scanning, such as, for example, magnetic resonance imaging decisions about scan planes, pulse sequences, and whether to use contrast agents; mammography, conventional X-ray examinations, nuclear medicine and positron emission tomography, ultrasound, bone density scanning, also called dual-energy x-ray absorptiometry (DEXA) or bone densitometry. The methods can also be applied to pathology testing techniques, such as, for example, histology, cytology, electron microscopy (EM), as well as techniques in cardiology, dermatology, opthalmology, and others.

Figure 7:
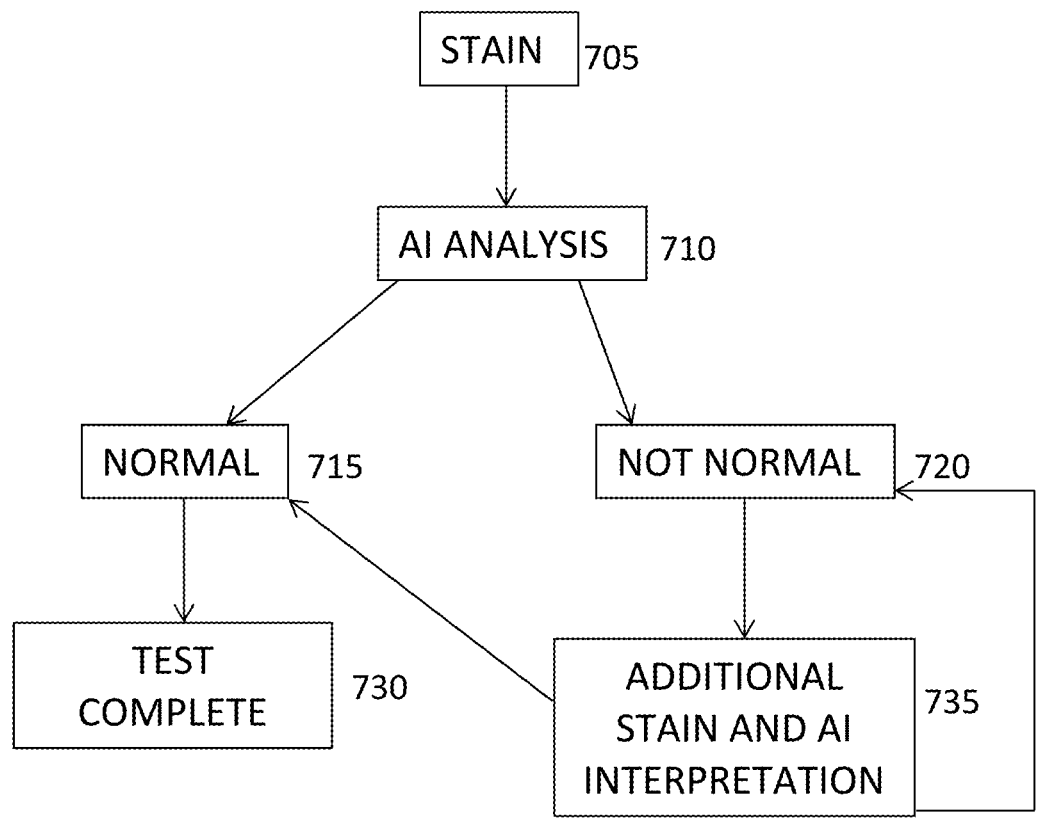

For example, FIG. 7 illustrates an embodiment of the methods of the present disclosure applied to biopsy tissue taken from a patient. For example, a hematoxylin and eosin stain (705) may be carried out, as known to the person of ordinary skill in the art. The stain results are then converted to a digital form to be interpreted by the AI (710), which may return a normal (715) or abnormal (720) categorization. In the normal case, the test may be considered complete (730). For the abnormal case, an iron stain of the tissue may be carried out by the laboratory technician, followed by AI interpretation of the iron stain (735). If this second AI interpretation returns a normal categorization, the medical test is complete. Otherwise, if the AI returns an abnormal categorization, an immunoglobulin stain may be carried out on the tissue, followed by a further AI interpretation. Each time, the results of the test may be digitized in order to input them into the AI algorithm. Following the immunoglobulin stain, if the categorization is still returned as abnormal, the report may be sent to a human doctor.

The methods described herein may be applied to any medical imaging technique where artificial intelligence is available and where there are different imaging protocols available handled by a technologist, such as, for example, radiological imaging including x-ray CT, magnetic resonance, mammography, archaeology, dermatology, or ophthalmology.

In some embodiments of the present disclosure, real-time refers to a time period that is short and allows further testing of a patient or tissue while the patient or tissue is still at the medical facility. For example, if a patient is undergoing a CT scan, the results are immediately processed and a recommendation for further scans is given with a short time, such that the patient is still present for further scans. For example, the patient may still be sitting in the scanning machine. For example, a short time may be a few minutes, such as less than 10 minutes or less than 5 minutes. In some embodiments, such short time for categorization may also be referred to as 'immediate', such that the AI categorization is available 'immediately'. In some embodiments, the medical imaging data analyzed by the AI is taken at a medical imaging facility. The AI may run on a computer present at the medical imaging facility, or the imaging data may be sent from the medical imaging facility, electronically, to the computer running the AI, which may be hosted on a server externally to the medical imaging facility. In both cases, the AI returns the results within a short time, such that the patient is still within the medical imaging facility, for example still located within the imaging apparatus (such as, for example, within an MRI machine). In some embodiment, the AI may prescribe collection of imaging data with a different technique, for example a different stain, or the use of a contrast, or may also prescribe the further scan to be limited to a region of the body part previously scanned, or the use of a higher resolution, such as thin slices instead of thick slices.

The methods may also have applications outside of the medic field, where the scanning protocol may benefit from optimization by immediate feedback of information related to the diagnostic content of the images produced.

The methods described herein allow specific recommendations and customizations of the scanning protocols. With more sophisticated AI, the exact type of the abnormality and its location may be specified in the information provided to the technologist. This would allow individually customized and more detailed appropriate imaging compared to returning a basic abnormal categorization. Some examples of particular AI diagnosis and the additional scanning are shown below.

If the AI detects a possible intracranial hemorrhage on the CT scan, it may recommend to perform axial thin CT slices through the abnormality. If the AI detects a possible possible pituitary mass lesion on MR scan, it may recommend to perform thin detailed MR images through the pituitary fossa. If the AI detects a possible abnormality at the inferior mayor margin of the CT scan, it may recommend to perform additional axial images extending inferiorly to cover the entire abnormality.

If the AI detects a possible intracranial mass lesion on CT, it may recommend to rescan following intravenous administration of intravenous contrast material. If the AI detects a possible melanoma on hematoxylin and eosin histological stains, it may recommend to prepare another sample of tissue using immunohistochemical stains.

As mentioned above, the artificial intelligence feedback loop to the scanning protocols is not limited to being a single loop. The AI system analysis may be reapplied after the first set of additional scans are obtained, for additional analysis and decision points.

Formalization

If $\{x\_i, =1, \ldots, N\}$ are N studies (each comprising a collection of images, and being in turn an array of positive numbers corresponding to the intensity of each pixel in each image), and y is a binary class variable, for instance y=0 for normal (negative) and y=1 for abnormal, then a classifier is a function y=f(x) that for any study x returns a binary value, for instance 0 if the study is negative or 1 if the study is positive. Sometimes the classifier is written in the form sign(f(x)), in which case f is known as the discriminant. For categorization, the class variable is not binary but instead belongs to a finite set y=1, M, of M diseases and their stage or severity. For detection/localization, the function f is defined at each voxel or pixel in each image x, where it returns a class label y. Detectors may also return bounding box coordinates, or perhaps a parametric curve.

For the case of binary classification, type-2 error (missed detection or false negative) refers to a classifier returning a value, for instance f(x)=0 (normal) when the true diagnosis is y=1 (abnormal). Type-1 error (false alarms, or false positive) refers to a classifier returning f(x)=1 (abnormal) when the true diagnosis is y=0 (normal). The cost of these two errors is usually different in medical diagnosis, as a type-1 error may cause un-necessary treatment but otherwise no major harm to the patient, whereas a type-2 error may have fatal consequences or result in malpractice suits. The performance of a classifier is measured by the average number of errors multiplied by the cost of each error, for example $c\_1$ for type-1 errors and $c\_2$ for type-2. This can be termed the (average) risk. A good classifier is one that minimizes risk.

The average entailed in the computation of risk is performed with respect to the probability of each type of error, leading to the expected risk. This process requires knowledge of the joint distribution p(x,y), which is usually unknown. However, a training set may be available, consisting of samples $(x_i, y_i)$ or p(x,y) of imaging studies $x_i$ with their "true" diagnosis $y_i$ (ground truth), for instance performed by a trained physician and double-checked by a second physician independently. Therefore, it is possible to compute the empirical risk, which is the sample approximation of the expected risk.

In Machine Learning, the classifier f is chosen from a class of functions, usually dependent on a set of parameters w, so f=f(x;w), which are chosen so as to minimize the risk. Ideally, it is desirable to minimize the expected risk, but since that is not known, it is possible to instead minimize the empirical risk, with the value of the risk at the minimum known as training error. Generally, there is no guarantee that a classifier minimizing the training error also minimizes the expected or test error: that is the error averaged over samples that are not included in the computation of the training error (and therefore not used in the determination of the parameters w). Indeed, it is possible for a classifier to make the training error small, and yet yield a high test error, a phenomenon known as overfitting. Much of the effort undergone during the past several decades in the fields of Machine Learning (ML), Pattern Recognition, and Statistical Inference has been to devise methods that, by means of minimizing the empirical risk or a regularized version thereof, are also guaranteed or at least empirically proven to yield good expected risk. Regularization refers to additional criteria, complexity constraints or bounds, or terms in a cost function that penalize certain solutions, see Ref. [31]. Regularization is now commonplace in machine learning and covered in textbooks, see Ref. [9].

Deep Learning (DL) is a subfield of ML whereby the function f(x;w) is implemented using a neural network (NN) with multiple hidden layers. A NN is a computational model that corresponds to a statistical graphical model whereby each "visible node" represents a measurement and each "hidden node" represents a random variable, with interconnections between nodes representing statistical dependency. Each node is meant to represent a "neuron" or neural computational unit, and performs linear operations (weighted averaging or convolution) of the output of connected neurons, followed by some kind of non-linearity operation, such as a sigmoidal function or rectified linear unit (ReLU) to yield the output. Neurons are typically connected between layers, but not within layers. However, there exist multiple architectures, so this particular choice should be considered as an example and not a limitation. The algorithm to minimize the empirical risk is a computationally efficient rendition of the chain rule (see Ref. [24]) and is known as "back-propagation". In other words, neural networks are a collection of algorithms, where computation is performed by discrete modules, or "neurons" (herein also termed "nodes"), using network parameters (weights) that are determined during a training phase so as to recognize patterns. Recently, deep convolutional networks have enjoyed a surge in popularity due to their performance in detecting, recognizing and categorizing objects in natural images, see Ref. [10]. Deep Learning can be understood as a collection of generic methods for function approximation, and in particular for approximations of an arbitrary discriminant given sufficient computational and training resources. Therefore, DL can be applied and has been applied to a variety of data sources and tasks. However, in the present disclosure the focus is on the use of DL for the analysis of medical images that have characteristics that are well suited, in particular, to deep convolutional neural networks (CNN). For finite computational and training resources, straightforward application of a CNN architecture designed for natural images does not take into account and exploit the particular restrictions imposed by medical images.

In deep learning, neural networks comprise multiple layers, with each layer comprising one or more nodes. For example, a neural network may comprise an input layer, a hidden layer, and an output layer. In some embodiments, the input layers may comprise input data, for example from a set of medical images. Subsequent, hidden layers may weigh values from the input layers according to a set of parameters and functions, and detect features in the data. In some embodiments, subsequent layers are able to detect increasingly complex features in the data. For example, if the data comprises human faces, some layers may detect small facial features and subsequent layers may combine the smaller facial features to detect a specific face.

In some embodiments, CNNs are feed-forward neural network. In other words, the layers feed their numerical values forward to subsequent layers, and do not create loops by feeding to previous layers. In other embodiments, other types of neural networks may be used.

In machine learning, a convolutional neural network is a type of feed-forward (or other type, e.g. recursive) artificial neural network in which the nodes respond to a specific input field. The input fields of different nodes can partially overlap. The output of an individual node to its input field can be computed mathematically by a convolution operation. A convolution operation is a mathematical operation on two functions which produces a third function. Generally, a convolution can be obtained integrating the pointwise product of the two functions, as a function of the relative translation between the two functions.

Deep Learning for Medical Imaging

The use of deep learning techniques in medical imaging is rather recent. In 2015, Medical Image Computing and Computer Assisted Intervention (MICCAI) conference—one of the premier conferences in medical imaging—featured a workshop on deep learning in medical imaging. For the most part, this consisted of the rote application of computational methods employed in natural images to medical images.

First, natural images are subject to nuisance variability such as scaling (any given object can project on a region of arbitrary size, from less than one pixel to the entire image, depending on where it is in space and the distance to the camera) and occlusion (only an arbitrary subset of an object, of arbitrary size and shape, can be visible depending on other objects occluding it) that are not present in medical images. In medical images, the voxel size or pixel size is typically known in metric units, and there are no occlusions. Instead, what is measured is absorption or density of tissue at each voxel. Furthermore, medical images are captured under controlled settings where, normally, the patient is approximately positioned in a pre-defined manner, so the data is naturally approximately registered and relatively translation-invariance of the classifier is not necessary the way it is in natural images where a given object can appear anywhere in the image. Therefore, the variability due to transformations of the image domain (the volume, or the imaging plane) can be largely attributed to intrinsic, as opposed to nuisance, variability.

Intrinsic variability refers to the inter-subject variability (the same healthy tissue may appear different in different subjects) and even intra-subject variability (the same patient may show differences in longitudinal studies taken at different instants in time, while still remaining within the bounds of the same class, for example the normal class). Similarly, in natural images, significant illumination changes have to be discounted as the same object can appear under direct illumination, cast shadow, multiple illumination sources, and the illuminant is in general unknown. In medical imaging, the probing signal is controlled, and therefore—except for global variability due to different sensor calibration or probing sequence design—the variability due to the transformation of the image range (the intensity or absorption) can be largely attributed to intrinsic variability. This is unlike natural images where the actual intensity of a pixel is largely irrelevant and contrast transformations are discounted by learning or design, through the use of contrast-invariant filters. In particular, in DL methods, such local contrast variability is "trained away" by presenting multiple images taken under different illumination, and is manifested in the contrast-invariant nature of the learned filters in the first layer. As it has been observed multiple times, first-layer filters resemble Gabor filter banks, which implement local regularized derivatives and are invariant or insensitive to contrast changes.

Additionally, medical images are typically samples of a volume, so the computational architecture of networks designed for the analysis of images, for instance convolutional neural networks (CNN), is not well adapted to them. Even though the filters and feature maps in CNNs are "three-dimensional", in the sense that filters and feature maps have two spatial dimensions plus one "channel" dimension, convolutions are performed by translating the filters along a planar domain. i.e., current CNNs perform two-dimensional convolutions of three-dimensional filters. Medical appearance features exist across three spatial dimensions; therefore it can be advantageous to process this data in three dimensions where these features exist. These requirements call for the development and utilization of techniques for three-dimensional convolutional neural networks (3DCNNs), that exploit the availability of volumetric data, and that enables its full use in the diagnosis. This method is unlike all prior known work in the use of deep learning for medical imaging, where individual slices in a volume are classified independently. Some existing works, making reference to 3D convolution components, apply patch-based volumetric classification. For example, Ref. [4], which fails to capture the global and context characteristics of the volume that are important for diagnosis. Other works utilize separable filters, see Ref. [28], thus forgoing the full power of CNNs to learn the most discriminative filters, or apply 3D convolution in a restrictive manner as part of an overall structure that is not fully 3D. Actual 3D Convolution-based NN have appeared only recently and only applied to the analysis of video data (see Ref. [3]) demonstrated in segmentation, optical flow estimation and video coloring. Video is fundamentally different to medical imaging volume as the three dimensions do not share a metric; the time-dimension is causal (there is an ordering), and the temporal statistics are substantially different from the spatial ones.

Furthermore, significant prior knowledge on the anatomical structures being imaged is available, some of which is represented in the training set, some of which is captured by generic regularizers (compactness and smoothness of the interface between anatomical structures), and some of which is encoded by knowledge of the anatomy. Such knowledge is available to trained professionals, and should not be discarded. These considerations call for the development and utilization of techniques for "deep supervision", whereby knowledge of anatomy and physiology can be exploited during the training phase of a deep network, beyond the simple supervision using binary (or multi-class) networks. No existing application of deep learning to medical imaging makes use of deep supervision in this manner. The only known use of deep supervision is Ref. [23]; that, however, is restricted to lung nodule classification.

Another issue relates to the fact that detection, classification, and categorization are closely intertwined, and significant prior knowledge of average or atlas shapes for anatomical structures is available. Because there are no occlusions, the prior anatomical knowledge can be used directly to facilitate localization and segmentation, without the complexities arising from scaling and occlusions. A conditional random field (CRF) regularization model, in conjunction with anatomic atlases and back-tracing of the locations (voxels) responsible for the highest-scoring label (see Refs. [7-8]), can be used to this end. A typical CNN framework has early layers that focus on high-resolution responses and late layers that compute outputs with coarse representations. This strategy leads to ambiguities in pixel-level and sub-pixel level labeling which leads to challenges in prognosis from radiology where small structures are more abundant than in natural images. Bringing small structures to the attention of radiologists is vital as these elements are more likely to be missed. No existing application of deep learning to medical imaging, apart the present disclosure, can provide localization or segmentation of the lesion responsible for the class returned by the deep network.

3DCNN

It is possible to apply 3DCNN on medical image volumes in an end-to-end fashion, such that large volumetric segments or entire image volumes can be used as input data for abnormality/anomaly detection and classification. These methods include voxel level prediction of annotations such as location, size, shape and anatomical labels. The method consists in the application of convolutional filters in three spatial dimensions, as opposed to the two spatial dimensions that are currently taught in standard CNNs. The challenge is in doing so in a computationally efficient manner, and in the application to the medical imaging domain. The preferred embodiments described in the present disclosure take advantage of recent progress in computational hardware (GPUs) and software (filter banks) to implement and train a fully 3D convolutional network (see Ref. [3]), but applied to the 3D imaging volume, as opposed to 2D space-and-time.

As known to the person of ordinary skill in the art, a convolutional network comprises multiple layers. Some of the layers are termed convolutional layers. An exemplary two dimensional convolution can be calculated as:

$$Y(x,y,n) = X(x,y,m)y,m) = \Sigma_i \Sigma_j \Sigma_m X(x-i,y-j,m) \cdot w_n(x,y,m) \qquad \text{eq. 1}$$

where Y is the output of a convolutional layer with N filters, X represents the output of the previous layer, x,y denote spatial coordinates, m denotes the $m^{th}$ channel in the input, n denotes the output channel from the $n^{th}$ filter. It can be noted that $w_n$ operates on all channels (m) at each spatial location to generate a new output with the same spatial dimensions as F, but only one output channel. Each layer can comprise several filters, producing several outputs, all of which are passed to subsequent layers as input. The outputs can be stacked together as channels and fed to the next layer.

An exemplary three dimensional convolution can be calculated as:

$$Y(x,y,z,n) = X(x,y,z,m) * w_n(x,y,z,m) = \Sigma_i \Sigma_j \Sigma_k \Sigma_m X(x-i,y-j,z-k,m) \cdot w_n(x,y,z,m) \qquad \text{eq. 2}$$

where Y is the output of a convolutional layer with N filters, X represents the output of the previous layer, x,y,z denote spatial coordinates, m denotes the $m^{th}$ channel in the input, n denotes the output-channel from the $n^{th}$ filter. It can be noted that $w_n$ operates on all channels (m) at each spatial location to generate a new output with the same spatial dimensions as F, but only one output channel. Each layer can comprise several filters, producing several outputs, all of which are passed to subsequent layers as input.

Deep Supervision

In some embodiments, deep supervision can be used by applying the same supervision at multiple stages of a network. In some embodiments, the methods of the present disclosure can apply the approach of Ref. [29] to medical images by using a different domain-specific deep supervision that differs from the classification goal. In other embodiments, since many factors influence clinical decision-making, it is possible to exploit these annotations (such as location, size, shape and anatomical atlases) by incorporating them through deep supervision that differs from the main classification/detection task. For example, certain abnormalities only exist in certain anatomies. Adding a deeply supervised output to localize this anatomy early in the network can help the detection of abnormalities in that region, e.g. using deep supervision to localize the liver aids in the detection of a liver disease. This can also be applied to age or gender related classifications, using deep supervision for key factors (such as those exhibited by young or old patients) can aid in the detection of abnormalities specific to those demographics.

Fine-Scale Localization and Segmentation

The methods of the present disclosure can apply a fine scale localization technique, similar to that described in Refs. [2, 34], which incorporates lower resolution features with higher resolution features to generate new higher resolution responses with the influence of multiple scales and coarse level guidance. The network architecture of the present disclosure utilizes typical (fine-to-coarse) network responses but adds additional structure such that coarse representations are directly incorporated with higher resolution features, generating new multi-scale features that benefit from large projective fields and abstract features (typical of a generic architecture), as well as fine-scale features. This embodiment incorporates both fine (narrow context, high resolution) and coarse (large context, low resolution) responses into a single representation, allowing fine scale detections, high-resolution pixels/voxels classification (segmentation) and image/volume classification of very small structures.

The methods of the present disclosure can apply the methods of Refs. [7,8,11], to medical imaging, allowing identification of which voxels in the input data have the strongest influence on the classification outcome of the neural network. The methods described in the present disclosure allow exploiting the same computations used to train the network (namely back-propagation) to instead find which voxels would have the largest impact on the class labels if modified. In more details, it is possible to compute the sensitivity of the class label to changes in value at each voxel (the partial derivative of the class label with respect to changes of value at each voxel), so that voxels that have very small sensitivity do not affect the class label. Highlighting voxels with high sensitivity value is a proxy to identify which data locations triggered a particular diagnosis by the network, and therefore may contain evidence for a disease.

In some embodiments, the images and the taxonomy of a set of medical images are copied in a database and physically stored in a medium, such as a computer. Reports, images and labels associated with the images can be stored in the database. For example, labels may be "normal" (no abnormalities), "clear" (no clinically significant abnormalities), or 'abnormal' (significant abnormalities). The abnormal class may be further categorized, for example in type and severity. These labels may be image/volume wide or include a detailed location of the pathology i.e. in which image, and which pixels/voxels in that image, including possibly a bounding box or even a curve outlining where the pathology is located physically in the body. Labels may also include a wide variety of fine-grained categories indicating the region/anatomy that is normal/abnormal, as well as different medical conditions associated with that abnormality. When necessary, fine-grained labels may also be combined on-the-fly into categories of similar pathologies, e.g. many different types of bleeds may be combined into a 'bleed' label for training purposes. This process does not destroy the underlying labels. In some embodiments, labels may be attached as metadata to the image files.

Pre-Processing

Traditionally, different images are often generated from the same raw data to highlight different tissues, for instance bone or soft tissue. In pre-processing, labels generated during training for one study can be propagated to different images corresponding to the same raw data. Similarly, labels provided for one imaging section (e.g. axial) can be propagated to different sections (e.g. sagittal, coronal), which creates additional labels in images that share physical location using a single annotation. The propagation of labels, during post-processing, can save computational resources as the neural networks do not need to generate again the same labels. This feature can be useful during training as well as during testing of the network.

In some embodiments, the raw data can be processed by a technician to provide labels that are easily interpreted by humans (e.g. bone kernel, soft tissue kernel). In other embodiments, the raw data can be processed directly by the system. For example, the 3D imaging volume, as opposed to axial, coronal, and sagittal sections, can be considered in a fully automated processing method.

The data can then be filtered using metadata to determine which images are axial, coronal, sagittal, and which images are corrupted or present significant artifacts. Images that contain artifacts or are corrupted are eliminated from the training set. If spurious images are detected, such as documents requested by the physician (e.g. dosage and other reports) or other non-relevant material, these images are filtered out and eliminated from the training set.

Individual images can be determined to be axial by inspecting the metadata of all images in its parent series. In some embodiments, two methods can be used for this purpose. The first method conducts a simple search of the metadata tags for the term 'xial'. For example, the tags (0020, 4000) and (0008, 0008) can be searched. The second method inspects the image spatial direction indicated by the metadata tag associated with the direction. For example, the tag (0020, 0037) can be inspected. If the spatial direction of any image within a series is within a specified value of the ideal axial direction (in relation to the patient position) the entire series (scan) can be considered axial.

As known to the person of ordinary skill in the art, DICOM is the standard format for medical imaging data. DICOM stands for Digital Imaging and Communications in Medicine standard, a standard format for medical imaging data and meta-data. In some embodiments, DICOM validation for the given images can be determined using two methods. The first method verifies that the four character code 'DICM' is present at position 128 in each DICOM file as required by the DICOM specification. In addition, the imaging data is inspected, and specific unresolvable errors may occur while reading the DICOM image using standard libraries. These errors can be: buffer read failure, undetermined image format, and a general load image error. If any of these errors are detected, the image data is considered corrupt.

Training

In some embodiments, a computer algorithm that implements one or more machine learning algorithms, for example as described above, can be used to process the training set. For example, as discussed above, the algorithm may comprise as a component a Deep Neural Network, and specifically a Convolutional Neural Network.

The neural network is designed to classify images into classes. During the training phase, images can be presented to the network together with the class label, and the network parameters are adapted so as to minimize a cost function. Upon completion of the training phase, at test time, an image is presented to the system. The system can apply the parameters learned during training, to produce an estimate of the class label for the new image. CNNs are designed to factor out nuisance variability, for instance due to illumination. As discussed above, in medical imaging, and especially, for example, CT, the intensity value of a pixel is informative and therefore it can be advantageous to modify the architecture to account for this feature. In some embodiments, the neural network can take advantage of the informative pixel intensity as discussed in the following. This may be obtained by excluding from the architecture the normalization operators that, in typical CNNs, are used to remove intensity information from the imaging data.

CNN architectures comprise a stacked set of processing modules including convolutions, rectification, nonlinearity, normalization, etc. In some embodiments, a CNN architecture that can advantageously analyze medical images comprises a first layer tasked with learning a single bias (offset) per pixel across the entire image (e.g. an image comprising 512×512 pixels). In typical CNNs, this "bias" is a fixed mean image applied during preprocessing. By contrast, in the present disclosure the CNN can learn this bias, thereby improving its performance compared to a typical CNN. In some cases, the images are scalar-valued (e.g. CT), in other cases the images are vector-valued (e.g. MR, proton density, diffusion coefficient, T1, T2, magnetic heterogeneity, etc.). In some embodiments, a CNN architecture, according to the present disclosure, can comprise a sequence of different types of layers, such as convolutions, rectified linear units (ReLU), and max pooling layers, followed by fully connected layers akin to GoogLeNet [Ref. 33]. As known to the person of ordinary skill in the art, GoogLeNet is a type of CNN comprising a plurality of different layers of nodes.

Convolutional layers in CNNs are typically the core building blocks of a CNN. The convolution layer's parameters consist of a set of learnable filters that can be trained to detect certain features in an image. Another type of layer in CNNs is pooling, which combines spatial neighborhoods using a non-linear operator and can optionally include down-sampling. Max pooling is a type of non-linear pooling, therefore the max pooling layers can be substituted by other types of non-linear pooling layers. In some embodiments, max pooling partitions the input image into a set of non-overlapping sub-regions and outputs the maximum of each sub-region. In some embodiments, pooling layers can be located in between convolutional layers or convolutions. Another type of layer comprises ReLUs, which can apply a non-saturating activation function. In neural networks, the activation function of a node defines the output of that node given an input or set of inputs. For ReLUs, an exemplary activation function is $f(x)=\max(0,x)$.

In some embodiments, a fully connected layer can be placed after several convolutional and max pooling layers. Neurons, or nodes, in a fully connected layer can have full connections to all activations in the previous layer. Another type of layer in CNNs is a loss layer, which specifies how the network training penalizes a deviation between the predicted and true labels. In some embodiments, the loss layer can be placed as a last, or close-to-last, layer in the CNN.

The architecture described above for an exemplary CNN represents the class of functions that are used to minimize the expected loss or other cost function, with respect to the free parameters, (such as the weights of the convolutional layers). In some embodiments, multinomial logistic loss is the cost function being minimized. However, the cost function can also be modified as described in the following.

In some embodiments, hinge loss can be applied, for mutually exclusive classes. Typically, the hinge loss refers to the threshold for a max(0,-) function. In some embodiments, multi-label tasks scores (where multiple classes may be present simultaneously) can be normalized with a probability simplex using a sigmoid function, followed by multi-label cross entropy loss. In other embodiments, scores are normalized using a soft-max function, followed by multinomial logistic loss. In some embodiments, combinations of these functions and loss functions are used, for example certain classes may be mutually exclusive and a soft-max function may be advantageous, whereas others may be independent and a sigmoid function may be suitable.

In some embodiments, the dataset can be divided into network training sets, network validation sets and clinical validation sets. All of these sets contain mutually exclusive studies, i.e. no part of a study may appear in two or more sets. For example, network training and validation sets are composed of images, or volumes (three-dimensional images), which are used to train and validate networks to correctly score inputs. The clinical validation set contains only study level labels, and it can be used to validate report generation only (see later for report description).

Figure 2:
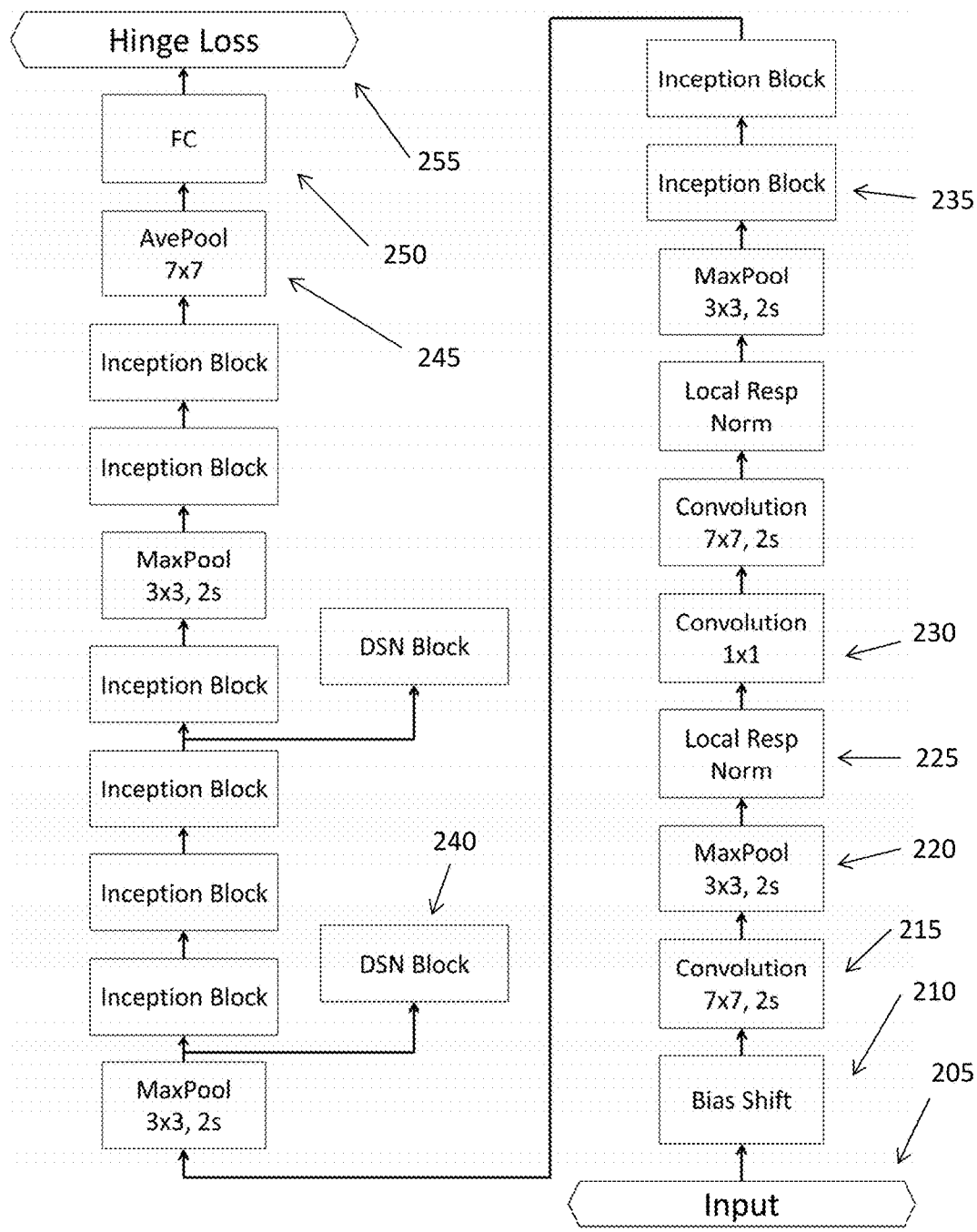
FIG. 2 illustrates an exemplary network architecture comprising several layers.

FIG. 2 illustrates an exemplary network architecture comprising several layers. In other embodiments, a different network comprising different layers may be used to detect and categorize medical anomalies. In the example of FIG. 2, the network starts with an input (205), for example 2D or 3D medical imaging data, followed by a bias layer (210). As described above in the present disclosure, CNNs normally include a fixed bias. However, the present disclosure, in some embodiments, describes how the bias can be learnt, instead, thereby improving the network performance applied to medical images.

The bias layer (210) is followed, in FIG. 2, by a convolutional layer (215). For example, a 7×7 convolutional layer (215) may be used. As known to the person of ordinary skill in the art, a layer has dimensions, for example a height and width for a 2D layer, expressed in pixels or neurons (spatial locations). A 7×7 layer will generally comprise 49 parameters. However, different layers having different dimensions and number of parameters may be used. In this example, layer (215) has a stride value of 2 ("2s"). As known to the person of ordinary skill in the art, the stride is the pixel shift across an image for each application of that specific layer's function. For example, a convolution for a convolutional layer, or a max pooling filter for a max pooling layer. In this example, layer (215) shifts by two pixels.

Figure 4:
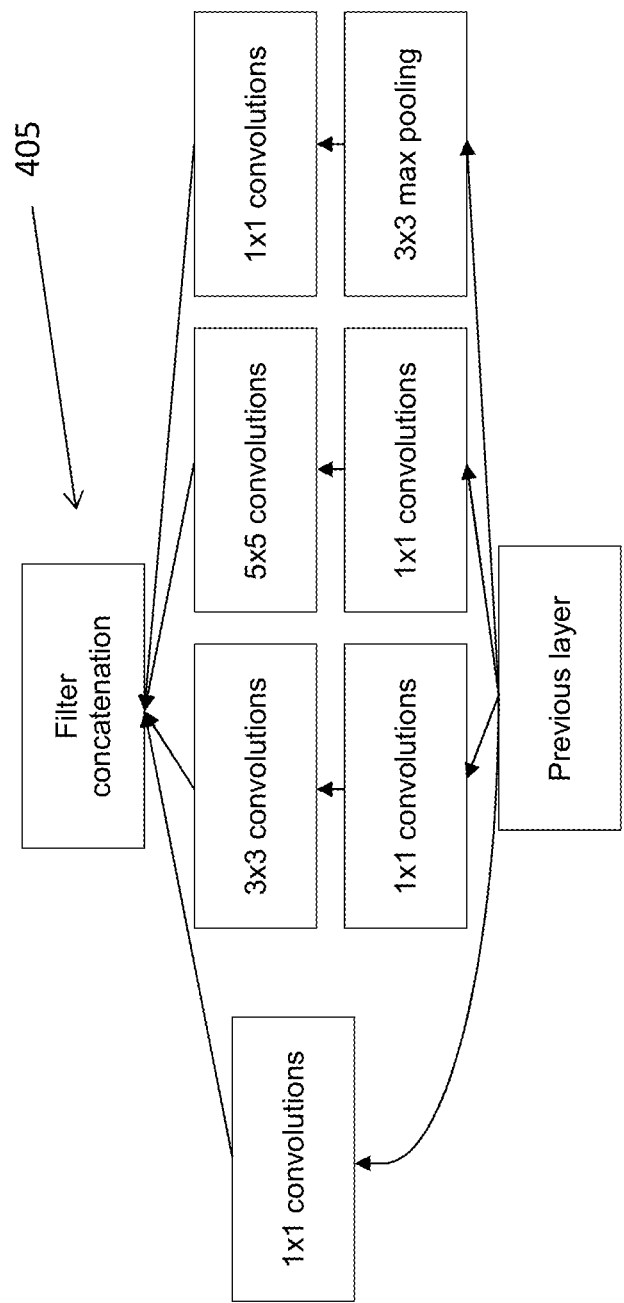
FIG. 4 illustrates an exemplary inception block.

Subsequent layers in FIG. 2 comprise a max pooling layer (220), with dimensions 3×3 and also a stride of 2. Other layers can comprise a local response layer (225), additional convolutional layers (230) and other building blocks of a network. For example, the inception block (235) represents multiple layers as described, for example, in FIG. 4. FIG. 4 comprises four different layer pathways, each having its own set of filters, the different layers converging into a filter concatenation (405) which stacks the outputs together. The exemplary inception block of FIG. 4 is discussed in Ref. 32. Other types of blocks may be used, as understood by the person of ordinary skill in the art.

The local response normalization layer (225) of FIG. 2 can perform "lateral inhibition" by normalizing over local input regions. For example, in the local response layer, each input value can be divided by $$(1+(\alpha/n)\Sigma_i x_i^2)^\beta \qquad \text{eq. 3}$$

where n is the size of each local region, $\alpha$ and $\beta$ are fixed parameters, $x_i$ is an input pixel, and the sum is taken over the region centered at that value.

In FIG. 2, the network comprises multiple inception blocks, as well as additional pooling layers, an average pooling layer (245), a fully connected layer (250), followed by hinge loss (255). The average pooling layer is similar to the max pooling layer, but uses an average instead of finding the max value. As understood by the person of ordinary skill in the art, hinge loss calculations can be used during training and testing of the network. If the training is ongoing, hinge loss can be calculated for each additional imaging data that is classified or categorized. However, if no training or testing is being carried out, the network can analyze the imaging data to return a class or category, without the hinge loss layer (255).

Figure 3:
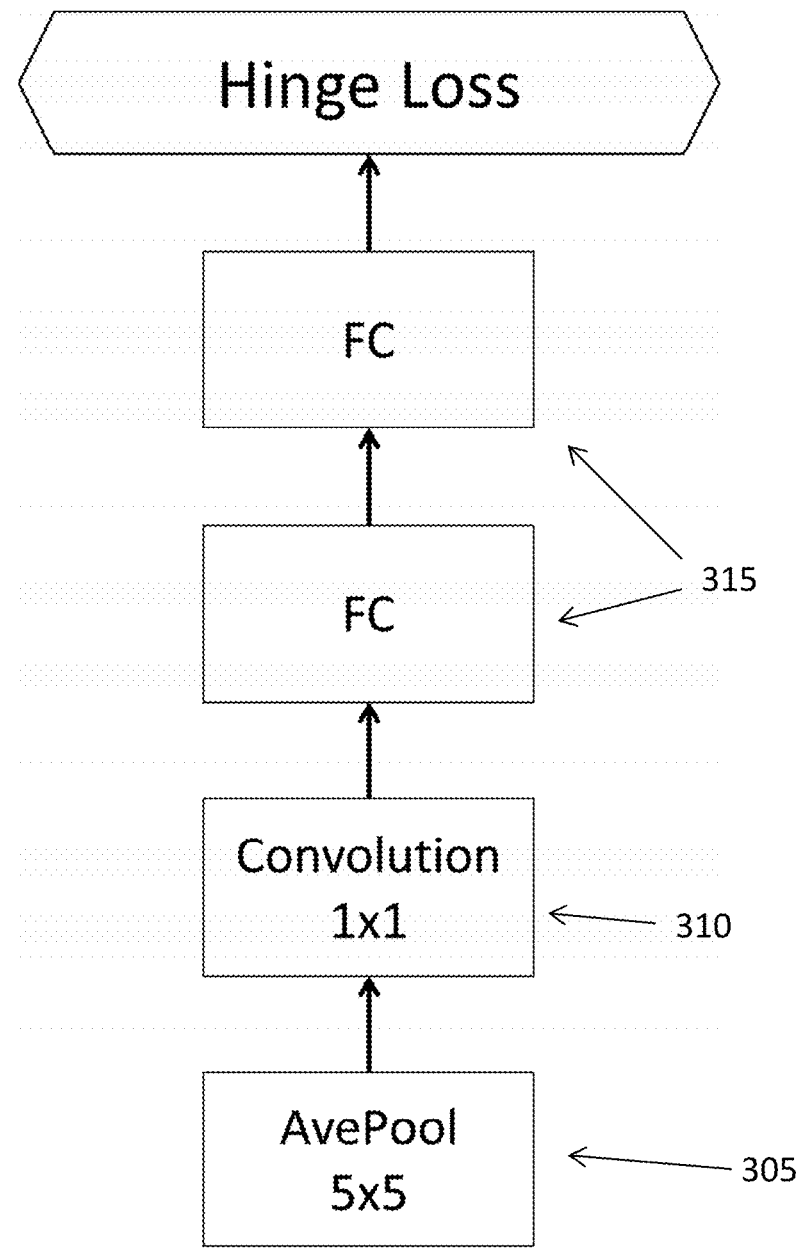
FIG. 3 illustrates an exemplary DSN block.

In embodiments using deep supervision, additional hinge loss layers can be used at intermediate depth of the network, for example in the deeply-supervised nets (DSN) block (240). DSN blocks carry out deep supervision to enhance training of the network. Hinge loss calculations determine whether the output of the network corresponds to the ground truth of the data. For example, if the imaging data contains a medical anomaly, the network should return a classification of the medical anomaly. If the output does not return the correct classification or categorization, the hinge loss calculation can back-propagate to adjust the network parameters in such a way as to return the proper classification for the medical data. Therefore, the hinge loss functions are used to adjust the network parameters, to optimize its performance and accuracy. The network can also be run with fixed parameters, after training, without back-propagation, that is with forward propagation only. In deep supervision, one or more DSN blocks can calculate hinge loss at intermediate depths. FIG. 3 illustrates an exemplary DSN block, comprising, for example, an average pooling layer (305), a convolutional layer (310), and two fully connected layers (315).

Data Augmentation

In some embodiments, in order to train the networks of the present disclosure to handle additional variation in data, it is possible to augment the data before training. Augmentation amounts to perturbing the available training data by applying to it nuisance transformations. In this manner, the network learns to be robust against such factors. For example, three types of simple augmentation can be applied to the data comprise scale, rotation and mirroring.

During training, each image may be modified by any combination of the following operations: 1) the image may be rotated by a specific angle, for example +/−25 degrees; 2) the image may be rescaled by a specific percentage, for example +/−10% of its original size; 3) the image may be mirrored. In some embodiments, the use of the specific values of +/−25 degrees and +/−10% is advantageous in augmenting the data, compared to other possible values for the rotation angle and the scaling factor. The values above were found to optimally simulate various patient positions and reduce position nuisance during training.

In some embodiments, 3D augmentation methods can be applied for both 3D and 2D training operations. If an abnormality in an image is localized (e.g. the center voxel is given), additional augmentation can be generated by out-of-plane rotation about a given physiologically acceptable point. This simulates patient movement, once coupled with translational insensitivity of the network architecture. This method can be used for 3D convolution training, while new 2D images can be generated through standard interpolation along a given axis (axial, coronal and sagittal). For example, it may be useful to apply a rotation about a point in 3D that would simulate the movement of the patient. For example, for imaging data referring to the head it may be advantageous to rotate an image about the base of the skull, in amounts similar to typical head movements.

Other augmentation methods may be used as necessary, through simulation of various artifacts, including ring artifacts, Poisson and Gaussian noise, beam hardening, beam scattering, edge effects, and out of field, reconstruction errors.

Balancing

Ordinarily, in deep learning based image classification, a roughly equal number of images for each class is presented. In some embodiments, since there is a preponderance of normal imaging data in medical images, the "clear" class can be deflated so as to achieve a balance of approximately 20%/80% rather than the actual average incidence. Since occurrence of many abnormalities in medical images is rare, and the physical space occupied by these pathologies may be small, e.g. one-two slices out of 100 in a study, there can be extreme class imbalances.

For example, given two classes, 'A' and 'B', in a given study, for a class to be considered 'A' all images must belong to the 'A' class, whereas class 'B' is inherited by the study when any image belongs to 'B'. For a given exemplary population, 10% of studies are class B and 60% are class A. For class 'B' studies, approximately 10% of images indicate 'B'. If a dataset contains 100 studies and all studies have 100 images, in a scenario where all images with known classes are used, the above percentages would lead to 6000 individual images in class A, and 100 images of class 'B'. This creates a ratio of 60:1 between class A and B.

Reducing the class imbalance in scenarios such as these can be handled through deflation of class A. In some embodiments, three methods for deflation can be applied to overrepresented classes: 1) restrict the number of over-represented labeled studies in each dataset, 2) reduce data augmentation on over-represented labeled images and 3) restrict the amount of data collected from each study from the over-represented class. For example, given the above scenario, only 50% of class 'A' studies and 10% of images in those studies would be trained on, at a time. As a consequence, a more manageable class balance of 5:1 between A and B can be achieved. In other embodiments, other methods to reduce class imbalances may be applied.

Ensembles

M some embodiments, an ensemble of networks may be trained, instead of a single network. These networks can be trained with the same data, and each network may perform slightly differently from the other networks. In some embodiments, the data may be modified to a greater or smaller degree, for each network. For example, small modifications of the data may comprise a reordering of the data, where the order refers to the sequence with which they are processed during training. An overall classifier can be obtained by averaging the results of each classifier in the ensemble of networks.

Balancing is a factor in how ensembles are built as well. In general, ensembles can be built by training the same or similar networks on the same data in a different order than other members of the ensemble. The ensemble generates a set of scores from each member in the ensemble, and scores can be aggregated together. The aggregation leads to a boost in performance, and decreases the effect of classifier noise.

In the ensembles of the present disclosure, an additional component relating to class balancing can be used when generating ensembles. Starting with an initial ensemble, new networks can be trained on data that generates inaccurate or uncertain scores from the current ensemble. This process can boost performance on difficult samples, without adding data that the system already processes accurately, while maintaining class balance as described above.

In addition, for the 3D and single 2D images, some network classifiers can use multiple spatially correlated slices as input for a single classification. Typically, CNNs use channels that represent different color spaces, e.g. RGB channels. Many classifications in natural images require color information to make a determination, however radiological images may require spatial context instead. This context could be added by selecting a number of neighboring images along the acquisition plane, or by using multiple images that share a point in 3D.

One possible method to capture spatial context comprises feeding small batches of adjacent images ("channels") to the image being processed. Similarly to the color processing of an RGB image, which comprises three images (one image per color channel, red, green and blue), it is possible to train a network with small batches of images. For examples, groups of three or more images may be used for each batch. A convolutional network normally performs two-dimensional convolutions, in the sense that filters are translated in two dimensions; however, the filters directed at capturing spatial context can span in three dimensions: two spatial dimensions and the third dimension comprising the "channels". A channel corresponds to a filter that performs a convolution on the layer's input. Given an image, convolution with each filter produces an output that has the same spatial dimensionality of the image (in two dimensions, x, y). A layer is composed of a collection of filters, and each filter provides one response map so that the complete output of the layer is comprised of each output for each filter leading to a layer output with an additional dimensions for each filter output, i.e. x,y,m, where x, y are the spatial dimensions of the input and m corresponds to the number of channels in the image. These channels are akin to RGB channels in natural images, where each channel represents different representations of the same image. In a RGB representation, each channel corresponds to the three chromaticities of the red, green, and blue.

Another possible method to capture spatial context comprises performing true 3D convolutions. This method is a generalization of the method above, where batches of images (possibly the entire volume of the study) are fed to the network but the filters translate in all three spatial dimensions. In other words, all three dimensions are treated equally. This implementation is more computationally intensive, both to train and to test.

As indicated above, ensembles of networks can produce more accurate scores than those produced by either one of the individual networks constituting the ensemble. However, producing scores for each network incurs additional computational costs. A single network can be trained to output the same scores as an ensemble through a process called 'knowledge distillation' [Ref. 33]. In this process, the network is trained to not only classify inputs, but also to produce scores that match those produced by an ensemble.

Application

In some embodiments, after the system is trained, the weights of the network are fixed, and the network is embodied as an algorithm running on a computer or server that receives as input new, previously unseen data (test set, or test datum), and produces an output.

In some embodiments, a study can be received and stored in memory. Metadata can also be stored. Whenever an image is received, the image is either added to a study or a new study is created. Once a new study is created, it can be queued for classification by the network. In some embodiments, the classification has a timer and can be blocked until there are no changes to the study for a given interval (e.g., 30 seconds). If the study is below a certain number of images, possibly indicative of a transmission or storage error, it can be rejected and not processed. Accepted studies are processed by the CNN, a series (scan/volume) at a time. The network computation may be distributed onto different computers. The classification can return raw scores for every image in a study. These scores can be saved on disk, in memory, or in a database.

M some embodiments, classification scores can be used in two ways: 1) a score is compared to a threshold, and if above the threshold, it is flagged for a particular classification, or 2) the maximum score across all scores may be used to flag each image. Depending on the type of classification, all images in the study may inherit that classification if one, some, or all images in a study are flagged with a particular classification. For example, if any image is flagged with a particular pathology, that flag may be inherited by the entire study. In contrast, only when all images in the study are flagged as 'normal' would the 'normal' flag be inherited by the study. In other words, if the pathology is visible in only one image of the study pertaining to a patient, the entire study can be classified as abnormal even though a subset of the images does not show the pathology.

In some embodiments, an algorithm can analyze the study-wide flags and produce an overall classification for the study as normal or abnormal. The algorithm can also categorize the nature of the abnormality in the report. Flags and categories can be derived from the taxonomy created by physicians in the taxonomy for the dataset. These taxonomies can be grouped into broad categories that relate to a particular physiology, and which are commonly used by human radiologists. These broad categories generally include, for example, 'BRAIN', 'SINUS', 'ORBIT', and 'BONES'. Flags from these categories may overlap with each other. These flags can be used to determine the details to be included in the reports, and the overall categorization of the report as normal or abnormal.

The output of the network can be transmitted to the report system that can use simple logic to generate a human readable report. For example, a simple lookup table can be used, which selects pre-formatted text based on the flags and categories assigned to that study and inserted into the report. Specific details are inserted into preformatted text where required, e.g. which image contains a particular abnormality or quantitative descriptions such as mass size in millimeters.

In the following, modifications of the algorithms described above for the case of real-time adaptation of protocols (as illustrated in FIGS. 5-7) are described. The machine learning algorithms described above are configured to work in an optimized way in a real-time configuration with reference to adjustment of real-time medical imaging. The exemplary methods described above can be modified accordingly, depending on the specific application. For example, the methods are described for a specific batch size, but other batch sizes may be used instead.

In a typical feed forward network, images are processed a single image at a time. Each image produces a single score vector. The network is trained by comparing this score vector with a target score vector, typically representing a human-assigned label. Images and labels are fed into a network where the terminal node produces a predicted score which is compared to the label input. This comparison generates loss/cost through some numerical function. This cost can be used to update the network parameters through back-propagation and an update process. Updates are usually carried out through an optimization method, such as gradient descent. When updating the network, it can be advantageous to get an accurate representation loss of the objective in the most general way possible. For this reason, networks are trained using a batch of images plus labels. This technique allows the estimation of the gradient of the network with greater accuracy.

Data flows through a network in the form of 'tensors'. A 2D image can be represented by three parameters: C (channels), H (height), and W (width), which form a tensor. The shape of this tensor would be, in this example, C×H×W. For example, a red-green-blue (RGB) color image that is 512 pixels wide and 512 pixels tall would form a 3×512×512 tensor, since the RGB representation has 3 channels. This tensor concept can be extended to N spatial dimensions, for example a 3D image could be 1×512×512×512 where the height, width and depth are 512. In the example of a 3D image, there is an added parameter, the depth.

The channel parameter, or dimension, is handled in a special way, and is required even if it collapsed to a value of 1. Channels can be used throughout the network to represent distinct outputs of layers. For example, if a 1×512×512 tensor passes through a convolution layer with M outputs, the result is an M×512×512 image.

As described above, data is processed by a network in batches, or groups of images. For example, a batch of images may correspond to a set of images taken during a single medical scan. This methodology adds a dimension to the tensors that are processed in a network. This dimension is pre-pended to the tensor dimensions, therefore N 2D images would be presented as a N×C×H×W tensor. For example, if the above 2D 512×512 example had a batch size of N=64, the resulting tensor would be 64×3×512×512. As the person of ordinary skill in the art will understand, different dimensions may be used, for example a different batch size or different pixel values for the image. For example, the image may comprise more pixels, or may not be a square image, and the batch size may be smaller or larger.

As previously described, the objective of the network during training is to produce scores for a given input image that match target scores (typically provided by annotation). To do this, the shape of the data tensor will change as it passes through the network, and at the terminal node of the network a vector with the desired number of scores is produced.

In this exemplary network, layers that produce M outputs would generate an N×M×H×W output. In a typical network, modifying the channel or spatial dimensions is allowed (and typical). Networks may spatially pool or otherwise down-sample tensors so that a tensor may have a smaller/lager spatial extent. An N×M×512×512 tensor may be spatially pooled by 2 to produce an N×M×256×256 tensor.

If the objective is to score 1×512×512 images with one of 10 scores, a vector with 10 dimensions is produced. If the batch size for this network is 64, the input tensor will have dimensions 64×1×512×512, and the final tensor will have dimensions 64×10. In this final tensor, a 'channel' represents one of the 10 scores for that image and there is one score vector for each of the 64 images resulting in a 64×10 tensor. It can be noted that, in typical networks known in the field of machine learning, each image is completely independent from its neighbors. The 'batch' siblings of each image have absolutely no effect on the score of each other image in the batch. Throughout the network, this first 'batch' dimension remains constant regardless of the changes to the other dimensions. However, in medical images, images in a batch are typically related. For example, the image may correspond to a scan of a part of the human anatomy. Therefore, adjacent images will be connected due to the anatomical feature of the part being scanned. The correlations between images in a batch can be taken into account by a network, as described in the present disclosure, to improve training and categorization results.

For the training process to work, all images are generally provided with a label. If an image does not have a label it does not contribute to the loss calculated by the cost function. Therefore, these images do not contribute to training or categorization. It is uncommon for images without labels to appear in training scenarios, and there is normally no advantage in applying computation time on images which cannot contribute to loss.

Figure 9:
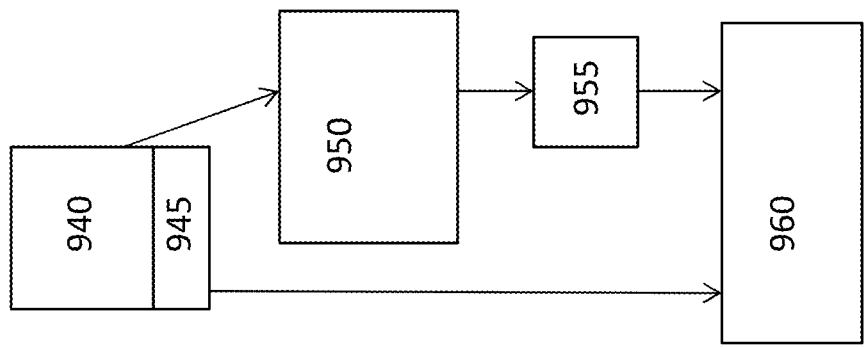
FIGS. 9-10 illustrate a typical network where the scores of neighboring images do not affect individual image scores.
Figure 9:
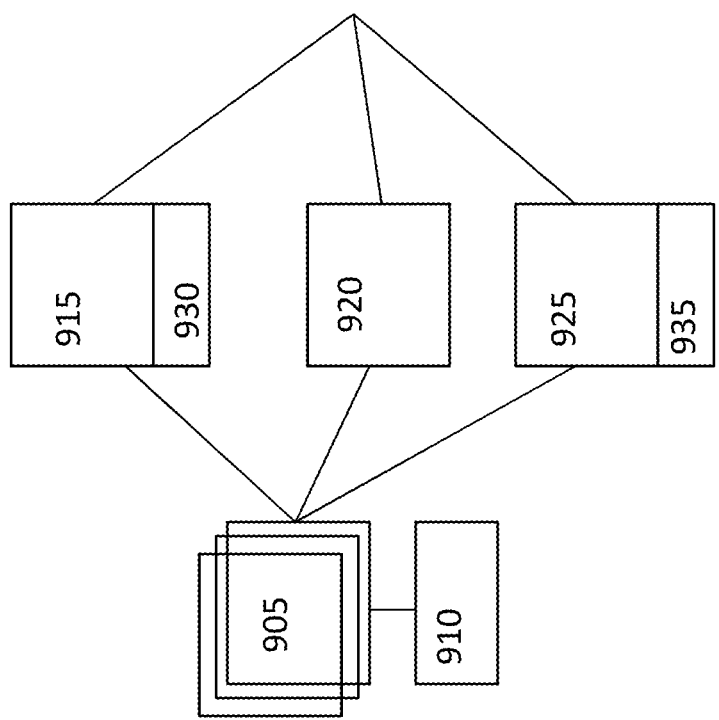

When using a network in an application, it is possible to generate scores for each image in the study (collection or batch of images) and use some method (e.g. thresholding) to decide if the likelihood of some abnormality is sufficiently high to mark each image with that abnormality. For example, if there are two possible scores, one score being NORMAL, the other being ABNORMAL, if the ABNORMAL score is greater than X, the image is said to be ABNORMAL. These assignments can be used to create an assignment for the entire collection of images. i.e. if one is ABNORMAL the entire set is ABNORMAL. There are other methods which use scores from a study to generate a score for the whole, such as decision trees or other types of aggregation, but all of these are normally carried out off-line and can only be used as a post processing step. FIG. 9 illustrates a typical network where the scores of neighboring images do not affect individual image scores. Study level labels are not used, and only images with labels are used.

In FIG. 9, a batch of images (905) has a study label for the batch (910), as well as images (915,925) with labels (930, 935) and images (920) without labels. The study label requires less human effort than the individual image labels. In this typical example known in the art, only images with labels are used. A CNN (950) is used to generate a score (955) for images (940) with labels (945), according to a loss function (960). For example, during training of the network, back propagation can be used, according to how far away from the truth (based on the cost function) the scores are from the known labels. Further, scores from neighboring images do not affect an image' score, and study labels are not used.

Figure 10:
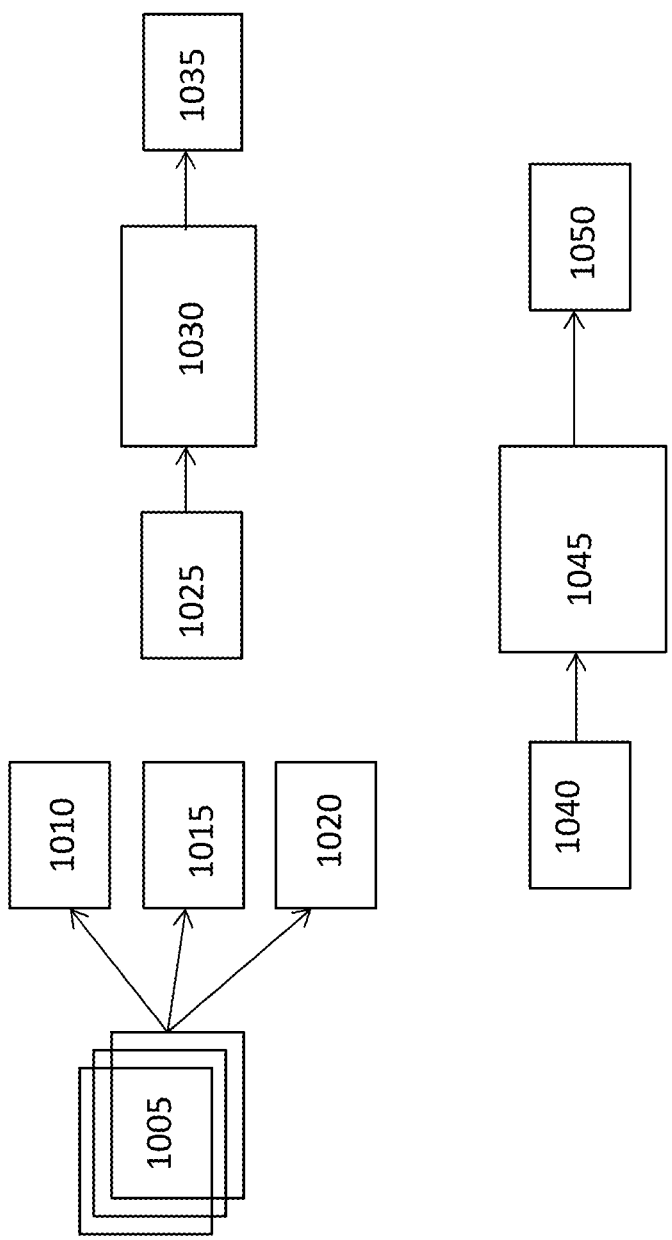

FIG. 10 illustrates multiple systems that are not connected. The systems are not connected end to end and are instead completely disjoint. In the example of FIG. 10, each image is examined in complete isolation from neighboring images. In FIG. 10, a batch (1005) of images (1010,1015, 1020) comprises, for example, 50 slides from a CT scan. The CNN (1030) analyzes the images (1025) and produces a score for each image. For example, if the batch (1025) comprises 64 images, the CNN will produce 64 scores (1035). The algorithm then collects all the image scores (1040), checks the individual scores (1045) and assigns a prediction for the study, generating a report (1050). The three systems are disjointed and not integrated, and each image is examined in isolation from the other images.

The typical approach to group of images as known to the person of ordinary skill in the art, for example as illustrated in FIGS. 9-10, is limited by the fact that inference on the collection/study labeling must be carried out outside the network. In other words, the machine learning algorithm is not coded to take into consideration, within the network and during scoring, the adjacent images in the group of images. Therefore, if a batch of images is input a traditional network, any correlation between adjacent images is neglected. This method can present a significant disadvantage when applied to a batch of images from a medical study, because of the inherent correlation between adjacent images, which can be used to improve scoring quality.

The limitations in traditional networks take a number of forms. During training, scores are completely disjoint. However, neighboring images could contain contextual cues that can aid in predictions for individual images. Many medical abnormalities exist across multiple images, and this context can be important in detecting the abnormality. Additionally, errors on individual images can be corrected through study-level analysis. The known methods require image-level labels for all images, and do not use study/collection level labels at all. During application, these limitations manifest as well. The typical system contains multiple disconnected subsystems and each image is examined in isolation. The system is therefore limited in making single image predictions and the network is not capable of learning labeling of the collection of images. To obtain a collection-level categorization, it is necessary to perform isolated analysis of the individual images, and subsequently to make inference judgments about the collection of images, through other means outside the network. This type of coding does not lend itself to real-time modification of testing protocols during medical exams, contrary to the algorithms described herein which take into consideration correlations between images in a batch.

Due to the fact that medical data is highly contextual, it is important to utilize this context and to code the utilization of these correlations within the algorithm of the machine learning network. In addition, training to the true objective is better than adding complexity after training. Therefore, training of a network which takes into account the correlations internally to the network will provide improved scoring compared to methodology comprising a network that does not take into account the correlations, coupled with post-processing which tries to take into account the correlations. The concept of training the network taking into account the correlations internally is termed herein as 'end-to-end'. In this approach, the end goal (the final application) matches as closely as possible the training.

Therefore, the methods described herein modify the typical data-flow within a network to incorporate the contextual information during training and application of the network. In order to do this, two modifications are carried out. The first modification is to reshape the tensor in a non-standard way, specifically to move the 'batch' dimension such that the data can be processed in a similar way as the other dimensions (e.g. channel or spatial dimensions). The second modification is to configure the network to be able to process data with a varying batch size, as the number of images in a collection/study is not consistent. For example, a medical test may obtain a certain number of images. However, a subsequent test of the same type may comprise a different number of images. For example, more images may be taken if a possible abnormality is tentatively detected.

Using the two modifications above, it is possible to train a network on entire studies, providing a number of advantages. For example, it is possible to move all external (study-level as opposed to image-level) inference into the network and train an end-to-end system. Additionally, it is possible to train on all images, even those without labels, as the feedback from the study level label is sufficient for scoring. Therefore, images without labels which are discarded in a system which does not take into account correlations between images internally to the machine learning algorithm, are instead taken into account in the methods described herein, which take into account correlations internally to the network. Therefore, the categorization returned by the network can be improved due to the additional data and information taken into account.

The advantages described above also lead to secondary advantages. Training an end-to-end system also allows an improved evaluation of the system, as the end-to-end implementation is much more efficient and provides much faster performance feedback as new algorithms are built. Using study level labels also allows training the networks with many more images without requiring specific image-level annotation. Study-level annotation is easier to obtain and this annotation is consistent with the normal work-flow of a typical radiologist, which in turns allows training networks with less human involvement and less radiologist-hour-cost.

In other words, a typical study will contain a study-level label as normal or abnormal, provided by a human radiologist. These studies are used to train a network to then be able to operate by analyzing studies not yet reviewed by a human radiologist. The performance of a network is improved by having additional studies available to train the network. If a typical study does not contain a label for each image, part of the study will have to be neglected. However, if the machine learning network is capable of training even if some images do not have a corresponding image-level label, by considering the study-level label, then the network can be trained better, and therefore provide improved analysis of subsequent studies.

Figure 11:
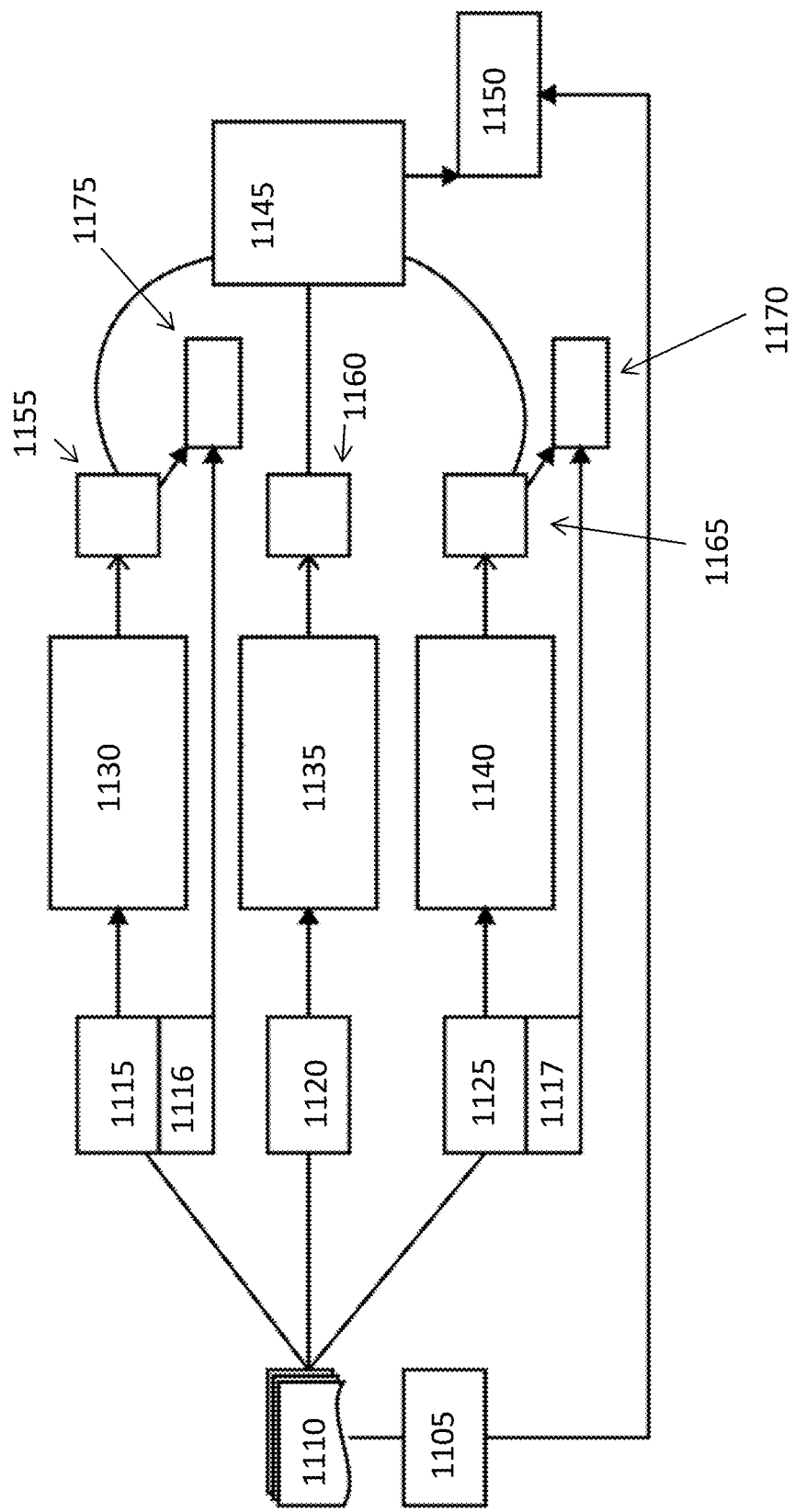
FIG. 11 illustrates a system where all images can be used, regardless of whether they possess an image-level label or only a study-level label.

For example, FIG. 11 illustrates a system where all images can be used, regardless of whether they possess an image-level label or only a study-level label. In the system of FIG. 11, neighboring images can influence each other, and study level labels can be used for additional feedback. In FIG. 11, for example, the score of one image can be boosted or reduced based on the scores of its neighbors. The reasoning behind this is that if an image includes an abnormality, it is likely that the abnormality is present in adjacent images since these represent adjacent regions of the anatomical part which was imaged. In FIG. 11, a batch (1110) of images has a study label (1105), with some images (1115,1125) having a label (1116,1117) and other images (1220) having no label. In FIG. 11, three CNNs are illustrated (1130,1135,1140), however a different number of networks may be used. In fact, the number of networks is variable and can be changed at every iteration during training and between studies. The networks generate scores (1155,1160,1165), with a loss calculation based on the image label (1175,1170) for those images which have labels. A module (1145) then combines the scores (1175,1170,1160), taking into account feedback between neighboring images, also accepting scores generated for images with no labels. A loss function (1150) takes into account the study label (1105). The configuration of FIG. 11 allows enhanced training and an improved performance of the system when generating a categorization for a new medical image study.

Figure 12:
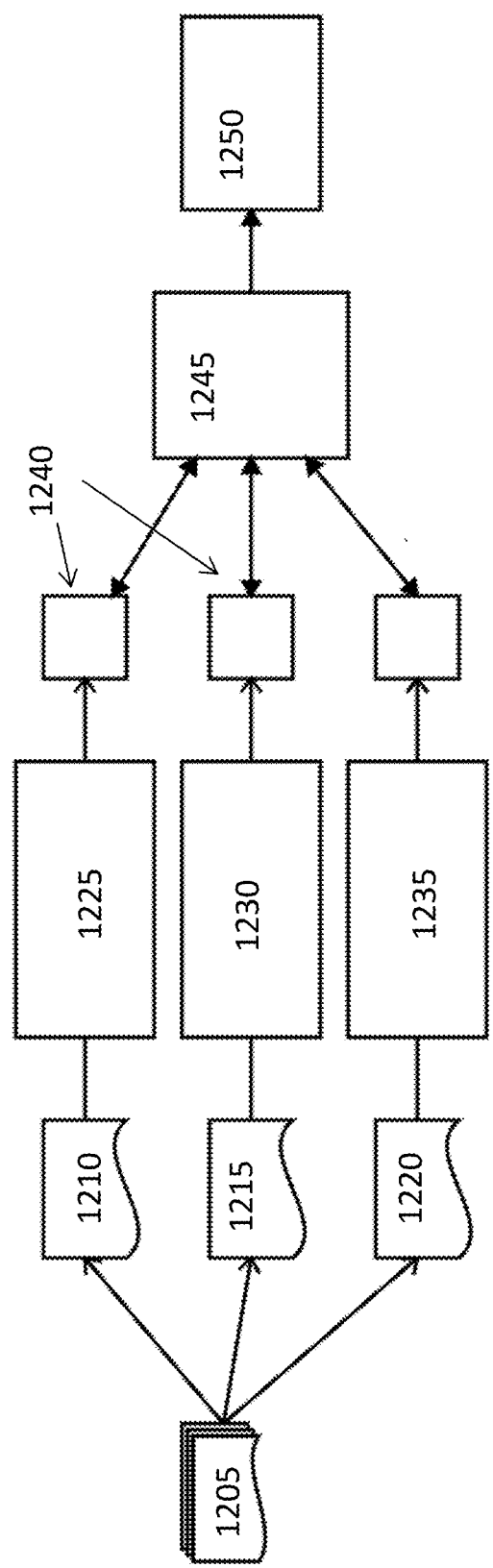
FIG. 12 illustrates an end-to-end system, where images are examined within the context of their neighbors.

FIG. 12 illustrates an end-to-end system, where images are examined within the context of their neighbors. Inference has been learned during training and builds on the context of the study. In FIG. 12, a study (1205) comprises multiple images (1210,1215,1220), analyzed by a variable number of networks (1225,1230,1235), generating scores (1240). The system combines scores and provides feedback from other images (1245) and assigns predictions (1250).

As described above, tensor reshaping is part of the modifications carried out on the machine learning algorithm to operate in real-time with a batch of correlated images. Tensor reshaping comprises changing how data is represented within the network, but does not require modifying the data itself.

As an example of tensor reshaping, it is possible to consider a 2D gray-scale image with height 512 and width 512 pixels. This tensor has been described above as a 1×512×512 tensor, but more accurately this is a 512×512 tensor with an extra singleton dimension. In fact, it is possible to represent this tensor with as many additional singleton dimensions as desired. A 512×512 tensor has the same amount of data as a 1×512×512 tensor, and the same amount of data as a 1×1×512×512 tensor, or any other 1×1×...1×512×512 tensor. For these tensors with the same data, only the representation has changed. This concept is applied within the network to add/modify tensor dimensions without modifying the data itself. Specifically, tensor reshaping is to replace/modify the 'batch' dimension so that the new representation allows processing across the batch. With this modification, the network is able to process information across the batch as if it were one of the other dimension types (channel or spatial).

Following the tensor reshaping, normal neural network operations can be used as if the data were a typically-represented tensor. Therefore, it is possible to apply a 'loss' function to an entire batch of data using only a single label, e.g. a study-level label.

A possible modification to apply tensor reshaping is to reshape at the end of the network, and 'push' the batch dimension by pre-pending a new singleton dimension. An example of this modification is described below and in FIG. 13, which illustrates an exemplary representation of a network using tensor reshaping to learn on an entire batch, and learn the contextual information within the batch. Tensor reshaping may also be carried out in different ways, i.e. not at the end of the network.

Tensor reshaping is a functionality that is available in typical neural network libraries as it is needed to modify C×H×W tensor dimensions. However, these reshape functionalities are not typically used to reshape the batch dimension and are not used to generate context across collections. Therefore, the methods of the present disclosure can apply the tensor reshaping available in network libraries for a different purpose as typically applied.

Variable batch size is another component modification that allows application of machine learning in real-time for adapting medical testing protocols. Studies from medical tests do not normally have a standard number of images, therefore it is advantageous to be able studies-as-batches, each study or batch having a different number of images. To carry out this modification, the data-input is allowed to govern the size and shape of the tensor. Additionally, during the forward execution, the required memory execution is allocated or bound. This modification allows processing of tensors each of which has a different size. Typically, varying image size is allowed during network execution, however these are typically used to process tensors with varying spatial dimensions, not varying batch dimensions. Therefore, the code allowing varying spatial dimensions could not typically allow a varying batch dimension.

In the following, some examples of methodologies related to those described above, as well as significant differences with the present disclosure are described.

Learning using only a single label for a batch is used by the person of ordinary skill in the art for multiple instance learning (MIL), sometimes called bag learning. In this scenario, only labels for the bag (batch) are known/used and a simple aggregation function (usually max) converts a set of score vectors to a single vector of scores. In Ref. [35], an example of bag learning with CNN for natural images is described. The main difference between the approach of Ref. [35] and that of the present disclosure is that that approach is limited to image labels, while in the present disclosure, 'bag' learning is used as a supplemental label, and the true objective function is to label the bag/batch. The approach of the present disclosure uses spatially (or other) correlated images and the objective is to not only learn scores for individual images, but also learn how those images interact with each other. This is the reason why additional learning structures are incorporate at the bag level.

Another approach would be to use a 3D network. This approach, however, can create a variety of problems, the principal of which are an exponential increase in parameters to learn, and the fact that not all studies comprise volumes (for example mammogram or ultrasound). More parameters can be computationally difficult, and this difficulty slows down learning significantly. When images are turned into volumes the number of examples to learn from is effectively reduced.

Variable sizes within a batch has also been used in networks where the size of each image is different (e.g some are 3×510×510, others are 3×496×496). Convolution is particularly robust to this type of size change, so it is natural to refrain from modifying aspect ratios for certain tasks. In these applications the batch size has always remained constant. In typical use cases, there is no need to use variable batch sizes. These implementations keep a fixed batch size and only check the other dimensions for changes. Example usages appear in the R-CNN methods as described in Refs. [36-38]. In the present disclosure, by contrast, all dimensions of the tensor are checked, and memory is reallocated as appropriate. Modifying the batch-size during training is not known to the person of ordinary skill in the art.

For example, the system may detect that the new study comprises 70 slides because the laboratory technician took 70 images. Therefore, the batch size is changed to 70 for this specific case. The memory required to handle the new batch size is calculated, and the network is rebound to reallocate the new memory requirements.

Figure 13:
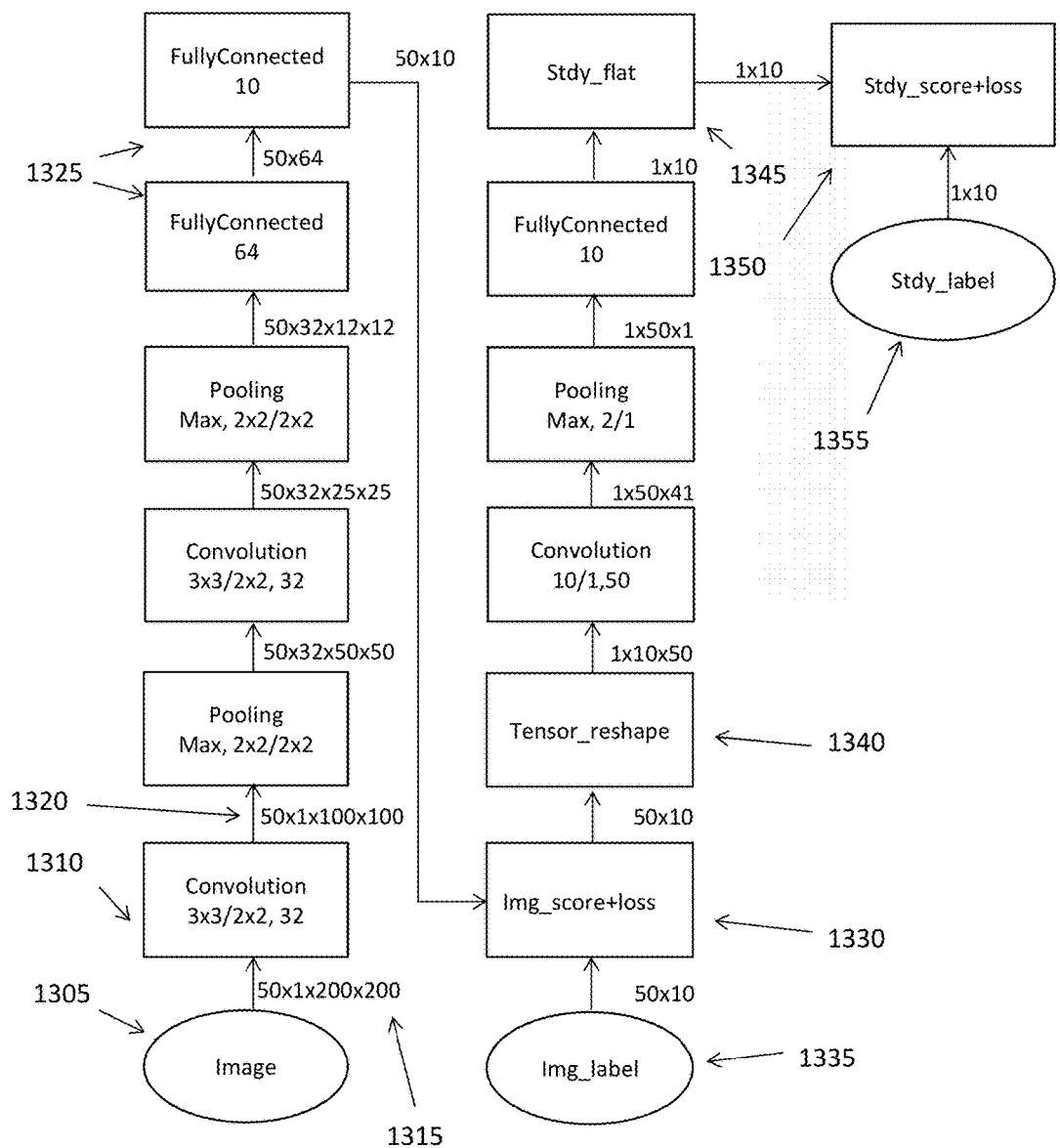
FIG. 13 illustrates an exemplary representation of a network using tensor reshaping to learn on an entire batch, and learn the contextual information within the batch.

FIG. 13 illustrates an exemplary network implementing tensor reshaping and study labels. The implementation of FIG. 13 is one possible embodiment, however any of the blocks or parameters in FIG. 13 may be modified according to the methods of the present disclosure.

In FIG. 13, an image or batch of images is an input (1305) for the network. Several convolution, max pooling and fully connected blocks comprise a first part of the network, similarly to the networks described in the present disclosure, for example with reference to FIGS. 2-4. For example, a first convolution block may have a 3×3 kernel, with a 2×2 stride, and 32 outputs (1310). The images input block (1305) can be described by parameters (1315), for example 50×1×200×200. As described above in the present disclosure, the first parameter may indicate an exemplary batch of 50 images, having a resolution of 200×200 pixels. The parameters associated with the batch of images may vary throughout the network processing. For example, in a subsequent step the spatial dimensions are halved to 100×100 pixels.

The fully connected layers have, in the example of FIG. 13, 64 outputs followed by 10 outputs (1325). In the second part of the network, the score and loss for each image in the batch can be calculated (1330), utilizing image labels (1335). For example, the image labels may be normal or abnormal, and the network is comparing the label with its own evaluation, determining the associated loss according to a cost function. In a following step, a tensor reshaping operation, as described in the present disclosure, can be carried out within the network (1340), followed by further convolution, max pooling and fully connected layers. In these layers, the kernel can be 1D instead of 2D, e.g. a kernel value of 10. These layers can carry out processing at the study level, determining a score for the study instead of single images in the batch.

An optional flattening block (1345) can flatten the input into a vector. The study score and associated loss can then be calculated (1350), based on a study label (1355). The study score and loss can be calculated without the flattening block (1345) as well.

In some embodiments, the network of FIG. 13 can be modified to include different or additional blocks. For example, after block (1340), scoring may be based also on additional types of data or metadata. For example, if the patient's medical current state or medical history is known, such data may be relevant to the diagnosis of the medical images, and may therefore be included to help train the network or to analyze the images with a trained network.

In some embodiments, tensor reshaping as carried out in (1340) may also, or alternatively, be carried out at different steps in the network, for example before or after block (1340). For example, the tensor may be reshaped at one step of the network, and subsequently reshaped to the original base.

Post-Processing

The medical inference integration layer software integrates the inbound DICOM image header metadata with the output of the neural networks applied to the images. This system produces a clinically appropriate output reflecting both the actual imaging data and the overall clinical situation of the patient. While there are many different possible embodiments for this post-processing stage, in general the concept relates to introducing a processing stage between the deep network and the decision stage, whether by a trained medical professional or the final patient. This stage can be designed and engineered exploiting user studies, human-computer interface studies, domain-specific knowledge, and natural language processing. In some cases, this post-processing stage includes visualization methods to enable the user to see through the volume, including but not limited to Virtual Reality (VR) displays, or navigation methods to traverse through the volume that is conformal to what is currently practiced by physicians and radiologists.

System Embodiments

The image data may be transferred from the medical imaging facility via VPN or SSL in a HIPAA compliant fashion to a central facility for processing by the integration medical inference engine and the deep learning networks. The clinically relevant interpretation of the data can be returned to the appropriate healthcare providers via the same secure method once the analysis is complete. Additional training and improvements of the system can be accomplished via periodic upgrades to the local software.

Alternatively, the integration medical inference and deep learning software may be installed locally on the medical imaging device or EMR system at the medical imaging facility and the analysis performed at the local facility. Additional training and improvements of the local system can be accomplished via periodic upgrades to the local software.

The output of the system may be communicated to an Emergency Department for assisted triage and to help expedite the treatment of the patient. Information may also be provided to the physicians signing off the report indicating specific images and location of pathology to assist the physicians to improve the report interpretation accuracy.

The system can generate revenue through fees charged for usage of the system by hospitals, clinics, physicians, patients, Medicare and insurance providers.

In yet another embodiment, the software running the CNN as well as the post-processing stage may be operated on a client device. As portable devices become increasingly powerful, and include dedicated processing units such as GPUs or DSP, processing could be performed locally at the end-user device (patient or medical professional). The entire system may run on mobile devices or be integrated into the imaging system for the convenience of the patient and local healthcare facilities. Additional training and improvements of the local system can be accomplished via periodic upgrades to the local software.

The system may be used on a social network allowing its members to upload medical images for a second opinion on their medical imaging study. In yet another embodiment, the software could be run though a social network, where patients can upload or link to the site of their data, and through the communication and computation infrastructure of a social network, such as those operate by Facebook™, Yahoo™, Amazon™, Google™, Microsoft™, or any other Cloud Computing service, the patients can receive a report or diagnosis or interpretation. In other words, the software in conjunction with cloud computing could provide a "second opinion" on data previously collected at a medical facility.

The training data can be collected from patient information from hospitals and clinics and always preserves all privacy laws including HIPPA.

The system can use feedback from physicians on the accuracy of its reports. The information is always transmitted in a secure fashion observing all privacy laws including HIPPA. This information can be used to further train the system for improved accuracy and performance.

When reviewing a report produced by the system for signature, the physician can make any changes prior to signing the report. These changes are captured and used to further improve the system by retraining.

The system can be designed to allow "lifelong learning" whereby errors detected by the system or by human professionals at any stage of the processing pipeline, all the way to errors that eventually result in patient harm or malpractice suit, can be fed back to the system and become part of the training set. In a particular embodiment, particularly challenging cases can be treated as "hard samples" and can be mined for training.

Regulatory Issues

In some embodiments, the present disclosure is implemented through a processor and memory configured to: receive imaging data relating to a body part of a human patient, for example a brain scan according to different medical techniques; classify the imaging data into a normal or an abnormal class; for the abnormal class, spatially localize an abnormality within the imaging data of the body part, for example the location of a tumor in the brain; and categorize the abnormality within a medical category, for example by categorizing the abnormality as a tumor, or a certain type of tumor. In some embodiments, the categorization can be carried out with standard medical categories, or it may also be carried out using non-standard categories. For example, categories can be created to categorize the abnormalities, with each category having specific information associated with it, such as the type or severity of the abnormality. In some embodiments, rotating an image is carried out by a rotation angle up to +/−50 degrees, and a scaling factor between +/−5% and +/−40%. The rotation angle may also be referred to as zero to 50 degrees, considering that the positive rotation can be redefined. The scaling factor can also be referred to as 5 to 40%, considering that the factor may be a reducing or magnifying factor.

Figure 8:
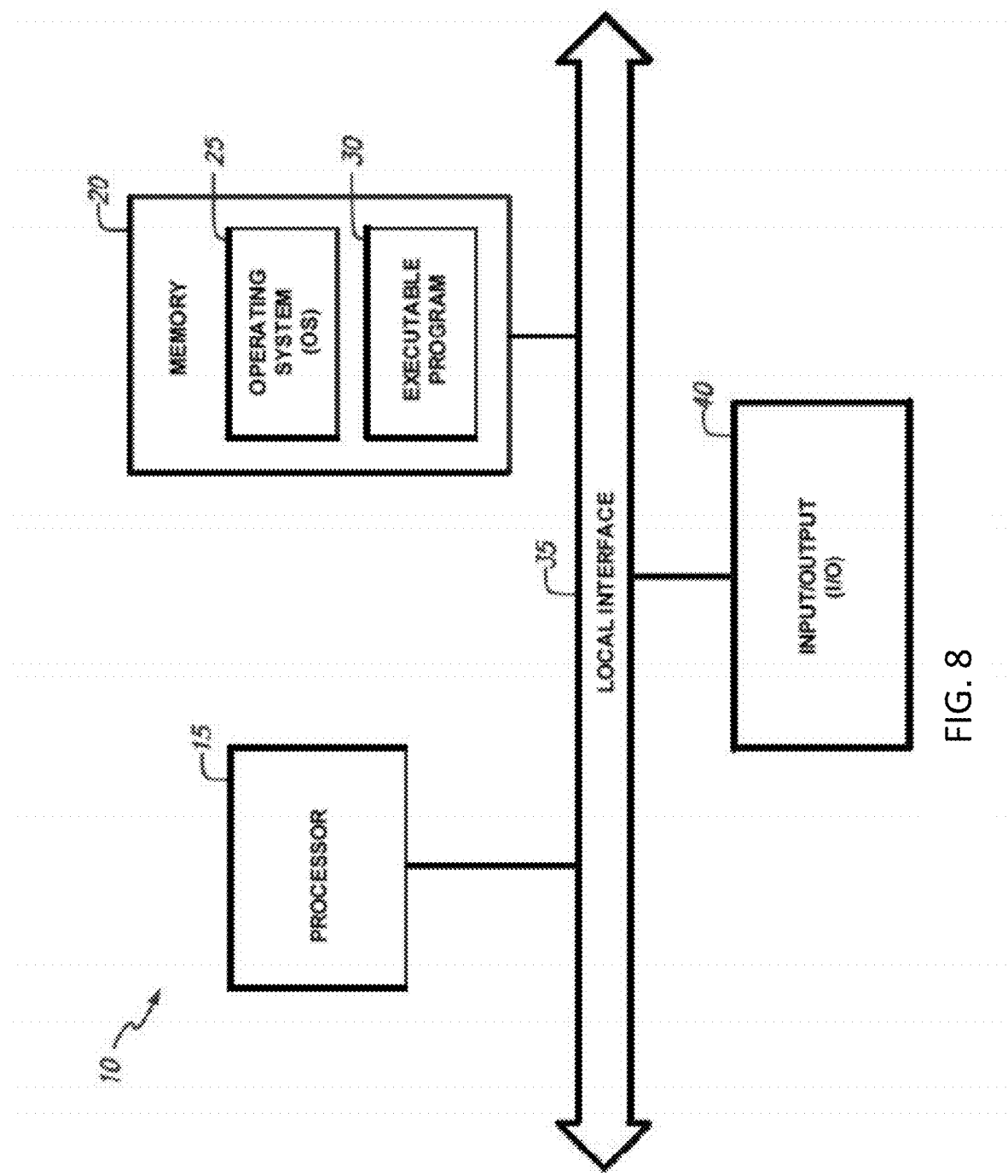
FIG. 8 depicts an exemplary embodiment of target hardware for implementation of an embodiment of the present disclosure.

FIG. 8 is an exemplary embodiment of a target hardware (10) (e.g., a computer system) for implementing the embodiments of FIGS. 1-4. This target hardware comprises a processor (15), a memory bank (20), a local interface bus (35) and one or more Input/Output devices (40). The processor may execute one or more instructions related to the implementation of FIGS. 1-4, and as provided by the Operating System (25) based on some executable program (30) stored in the memory (20). These instructions are carried to the processor (15) via the local interface (35) and as dictated by some data interface protocol specific to the local interface and the processor (15). It should be noted that the local interface (35) is a symbolic representation of several elements such as controllers, buffers (caches), drivers, repeaters and receivers that are generally directed at providing address, control, and/or data connections between multiple elements of a processor based system. In some embodiments the processor (15) may be fitted with some local memory (cache) where it can store some of the instructions to be performed for some added execution speed. Execution of the instructions by the processor may require usage of some input/output device (40), such as inputting data from a file stored on a hard disk, inputting commands from a keyboard, inputting data and/or commands from a touchscreen, outputting data to a display, or outputting data to a USB flash drive. In some embodiments, the operating system (25) facilitates these tasks by being the central element to gathering the various data and instructions required for the execution of the program and provide these to the microprocessor. In some embodiments the operating system may not exist, and all the tasks are under direct control of the processor (15), although the basic architecture of the target hardware device (10) will remain the same as depicted in FIGS. 1-4. In some embodiments a plurality of processors may be used in a parallel configuration for added execution speed. In such a case, the executable program may be specifically tailored to a parallel execution. Also, in some embodiments the processor (15) may execute part of the implementation of FIG. 1, and some other part may be implemented using dedicated hardware/firmware placed at an Input/Output location accessible by the target hardware (10) via local interface (35). The target hardware (10) may include a plurality of executable programs (30), wherein each may run independently or in combination with one another.

The methods and systems described in the present disclosure may be implemented in hardware, software, firmware or any combination thereof. Features described as blocks, modules or components may be implemented together (e.g., in a logic device such as an integrated logic device) or separately (e.g., as separate connected logic devices). The software portion of the methods of the present disclosure may comprise a computer-readable medium which comprises instructions that, when executed, perform, at least in part, the described methods. The computer-readable medium may comprise, for example, a random access memory (RAM) and/or a read-only memory (ROM). The instructions may be executed by a processor (e.g., a digital signal processor (DSP), an application specific integrated circuit (ASIC), a field programmable logic array (FPGA), a graphic processing unit (GPU) or a general purpose CPU.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

The references in the present application, shown in the reference list below, are incorporated herein by reference in their entirety.

REFERENCES

[1] Lee et al., C.-Y. Lee, S. Xie, P. Gallagher, Z. Zhang, and Z. Tu. Deeply-supervised nets. AISTATS, 2015.

[2] Honari et al., S. Honari, J. Yosinski, P. Vincent, and C. Pal, "Recombinator Networks: Learning Coarse-to-Fine Feature Aggregation," arXiv.org, vol. cs.CV. 23 Nov. 2015.

[3] Tran et al., Du Tran, L. Bourdev, R. Fergus, L. Torresani, and M. Paluri, "Deep End2End Voxel2Voxel Prediction," arXiv.org, vol. cs.CV. 20 Nov. 2015.

[4] M. Lai. Deep Learning for Medical Image Segmentation. arXiv.org, vol. cs.LG. 8 May 2015.

[5] Wang et al., 2015: L. Wang, C.-Y. Lee, Z. Tu, S. Lazebnik. Training Deeper Convolutional Networks with Deep Supervision. ArXiv 1505.02496, May 11, 2015.

[6] Merkow et al. "Structural Edge Detection for Cardiovascular Modeling." *Medical Image Computing and Computer-Assisted Intervention—MICCAI* 2015. Springer, 2015. 735-742.

[7] A Mahendran, A Vedaldi—Understanding deep image representations by inverting them, arXiv preprint arXiv:1412.0035, 2014

[8] K Lenc, A Vedaldi—Understanding image representations by measuring their equivariance and equivalence, arXiv preprint arXiv:1411.5908, 2014

[9] K. P. Murphy. Machine Learning, a Probabilistic Perspective. MIT Press, 2012.

[10] A Krizhevsky, I Sutskever, G E Hinton, Imagenet classification with deep convolutional neural networks, Advances in neural information processing systems, 1097-1105, 2012

[11] A Kirillov, D Schlesinger, W Forkel, A Zelenin, S Zheng, P Torr, C Rother, A Generic CNN-CRF Model for Semantic Segmentation, arXiv preprint arXiv:1511.05067, 2015

[12] D. E. Rumelhart, G. E. Hinton, R. J. Williams. Learning representations by back-propagating errors. Nature 323, p. 533-536, 1986.

[13] Saver J L, Fonarow G C, Smith E E, Reeves M J, Grau-Sepulveda M V, Pan W, Olson D M, Hernandez A F, Peterson E D, Schwamm L H. Time to treatment with intravenous tissue plasminogen activator and outcome from acute ischemic stroke. JAMA. 2013 June; 309(23): 2480-8

[14] Bershad E M, Rao C P, Vuong K D, Mazabob J, Brown G, Styron S L, Nguyen T,

[15] Delledera E, Smirnakis S M, Lazaridis C, Georgiadis A L, Mokracek M, Seipel T J,

[16] Nisbet J J, Baskaran V, Chang A H, Stewart P, Suarez J I. Multidisciplinary protocol for rapid head computed tomography turnaround time in acute stroke patients. J Stroke Cerebrovasc Dis. 2015 June; 24(6): 1256-61

[17] Gunn A J, Mangano M D, Pugmire B S, Sahani D V, Binder W D, et al. Toward Improved Radiology Reporting Practices in the Emergency Department: A Survey of Emergency Department Physicians. J Radiol Radiat Ther 2013 1(2): 1013

[18] Alexander J. Towbin, Srikant B. Iyer, James Brown, Kartik Varadarajan, Laurie A. Perry, David B. Larson. Practice Policy and Quality Initiatives: Decreasing Variability in Turnaround Time for Radiographic Studies from the Emergency Department. RadioGraphics, March 2013, Vol. 33: 361-371, 10.1148/rg.332125738

[19] Wong W S1, Roubal I, Jackson D B, Paik W N, Wong V K, Outsourced teleradiology imaging services: an analysis of discordant interpretation in 124,870 cases, J Am Coll Radiol. 2005 June; 2(6):478-84.

[20] Brady A, Laoide R Ó, McCarthy P, McDermott R. Discrepancy and Error in Radiology: Concepts, Causes and Consequences. The Ulster Medical Journal. 2012; 81(1):3-9

[21] Pinto A, Brunese L. Spectrum of diagnostic errors in radiology. World Journal of Radiology. 2010; 2(10):377-383. doi:10.4329/wjr.v2.i10.377

[22] Engl, Heinz Werner, Martin Hanke, and Andreas Neubauer. Regularization of inverse problems. Vol. 375. Springer Science & Business Media, 1996.

[23] W. Shen, M. Zhou, F. Yang, C. Yang, and J. Tian, "Multi-scale Convolutional Neural Networks for Lung Nodule Classification," in IPMI, 2015

[24] Rumelhart et al., Learning internal representations by error propagation, Parallel distributed processing: explorations in the microstructure of cognition, vol. 1, pages 318-362, MIT Press Cambridge, Mass., USA, 1986

[25] Du Tran, L. Bourdev, R. Fergus, L. Torresani, and M. Paluri, "Deep End2End Voxel2Voxel Prediction," arXiv.org, vol. cs.CV. 20 Nov. 2015.

[26] H. R. Roth, L. Lu, A. Farag, H. C. Shin, and J. Liu, "DeepOrgan: Multi-level Deep Convolutional Networks for Automated Pancreas Segmentation," arXiv.org. 2015.

[27] W. Shen, M. Zhou, F. Yang, C. Yang, and J. Tian, "Multi-scale Convolutional Neural Networks for Lung Nodule Classification," IPMI, 2015.

[28] Y. Zheng, D. Liu, B. Georgescu, H. Nguyen, and D. Comaniciu, "3D Deep Learning for Efficient and Robust Landmark Detection in Volumetric Data"

[29] K. Lee, A. Zlateski, V. Ashwin, and H. S. Seung, "Recursive Training of 2D-3D Convolutional Networks for Neuronal Boundary Prediction," Advances in Neural Information Processing Systems, 2015, pp. 3559-3567.

[30] K. He, X. Zhang, S. Ren, and J. Sun, "Deep Residual Learning for Image Recognition," arXiv.org, vol. cs.CV. 10 Dec. 2015.

[31] Engl, Heinz Werner, Martin Hanke, and Andreas Neubauer. Regularization of inverse problems. Vol. 375. Springer Science & Business Media, 1996

[32] Szegedy, Christian, et al. "Going deeper with convolutions." Proceedings of the IEEE Conference on Computer Vision and Pattern Recognition. 2015.

[33] Hinton, Geoffrey, Oriol Vinyals, and Jeff Dean. "Distilling the knowledge in a neural network." arXiv preprint arXiv:1503.02531, 2015.

[34] Merkow, Jameson, David Kriegman, Alison Marsden, and Zhuowen Tu. "Dense Volume-to-Volume Vascular Boundary Detection." International Conference on Medical Image Computing and Computer-Assisted Intervention. Springer International Publishing, 2016.

[35] M. Sun, T. X. Han, M.-C. Liu, and A. Khodayari-Rostamabad, "Multiple Instance Learning Convolu-tional Neural Networks for Object Recognition," arXiv.org, October 2016.

[36] R. Girshick, J. Donahue, T. Darrell, and J. Malik, "Rich feature hierarchies for accurate object detection and semantic segmentation," in *Computer Vision and Pattern Recognition,* 2014.

[37] R. Girshick, "Fast r-cnn," in *International Conference on Computer Vision (ICCV),* 2015.

[38] S. Ren, K. He, R. Girshick, and J. Sun, "Faster R-CNN: Towards real-time object detection with region proposal networks," in *Advances in Neural Information Processing Systems (NIPS),* 2015.

What is claimed is:

1. A device comprising:
a processor and memory configured to implement the steps of:
receiving imaging data relating to a body part of a human patient, taken at a medical imaging facility;
classifying by machine learning the imaging data into a normal or an abnormal class;
if the imaging data is classified as abnormal, suggesting collection of additional imaging data of the body part while the human patient is still present at the medical imaging facility;
for the abnormal class, spatially localizing an abnormality within the imaging data of the body part;
categorizing by machine learning the abnormality within a category; and
implement computer code of a convolutional neural network (CNN), the CNN comprising a plurality of layers in a sequence, each layer comprising a plurality of nodes, wherein:
each node of each layer is connected to at least one other node of a subsequent or preceding layer in the sequence,
each node accepts an input value and outputs an output value,
the classifying, spatially localizing and categorizing are by the CNN,
the imaging data comprises a training set of correctly diagnosed imaging data, the nodes in the CNN comprise parameters, and the CNN is trained on the training set to optimize the node parameters,
the plurality of layers comprises convolutional layers, rectified linear unit layers, non-linear pooling layers and fully connected layers, and
the non-linear pooling layers are max pooling layers that partition at least one image of the imaging data into non-overlapping sub-regions and output a maximum value for each sub-region.

2. The device of claim 1, wherein the CNN is trained by deep supervision based on known anatomy of the body part.

3. The device of claim 2, wherein:
the imaging data is three-dimensional and comprises anatomical annotations, and
the CNN is a three-dimensional CNN (3DCNN) trained to recognize three-dimensionality of the imaging data, and exploit the anatomical annotations.

4. The device of claim 3, wherein the imaging data comprises a set of images, the classifying comprises assigning a normal or abnormal label to at least one image of the set, and the label is propagated by the computer to at least one other image of the set previously without label.

5. The device of claim 1, wherein the imaging data comprises X-ray slides, computerized tomography, magnetic-resonance, diffusion-tensor (DT), functional MR, gene-expression data, dermatological images, or optical imaging of tissue slices.

6. The device of claim 1, wherein prescribing collection of additional imaging data comprises specifying a region of the body part and limiting the additional imaging data to the specified region.

7. The device of claim 1, wherein prescribing collection of additional imaging data comprises prescribing a different imaging technique or prescribing collection at an increased resolution.

8. The device of claim 1, wherein the processor and memory are further configured to repeat the steps of: receiving imaging data, classifying by machine learning the imaging data, and suggesting collection of additional imaging data.

9. A method comprising:
receiving, by a computer, imaging data relating to a body part of a human patient;
classifying by machine learning the imaging data into a normal or an abnormal class;
if the imaging data is classified as abnormal, suggesting collection of additional imaging data of the body part while the human patient is still present at the medical imaging facility;
implementing in the computer a convolutional neural network (CNN), the CNN comprising a plurality of layers in a sequence, each layer comprising a plurality of nodes, wherein:
each node of each layer is connected to at least one other node of a subsequent or preceding layer in the sequence,
each node accepts an input value and outputs an output value,
the classifying, spatially localizing and categorizing are by the CNN,
the plurality of layers comprises convolutional layers, rectified linear unit layers, non-linear down-sampling layers and fully connected layers, and
the non-linear down-sampling layers are max pooling layers;
partitioning, by the max pooling layers, at least one image of the imaging data into non-overlapping sub-regions; and
outputting a maximum value for each sub-region.

10. The method of claim 9, further comprising for the abnormal class, spatially localizing by machine learning an abnormality within the imaging data of the body part.

11. The method of claim 10, further comprising categorizing by machine learning the abnormality within a category.

12. The method of claim 9, wherein the imaging data comprises a training set of correctly diagnosed imaging data, the nodes in the CNN comprise parameters, and further comprising optimizing the node parameters by training the CNN on the training set.

13. The method of claim 9, further comprising training the CNN by deep supervision based on known anatomy of the body part.

14. The method of claim 13, wherein the imaging data is three-dimensional and comprises anatomical annotations, the CNN is a three-dimensional CNN (3DCNN), and further comprising training the 3DCNN to recognize three-dimensionality of the imaging data and exploit the anatomical annotations.

15. The method of claim 9, wherein the imaging data comprises a batch of images, the classifying comprises assigning a normal or abnormal label to at least one image of the batch, and further comprising propagating the label to at least one other image of the batch previously without label.

16. The method of claim 9, wherein the imaging data comprises X-ray slides, computerized tomography, magnetic-resonance, diffusion-tensor (DT), functional MR, gene-expression data, dermatological images, or optical imaging of tissue slices.

17. The method of claim 9, wherein prescribing collection of additional imaging data comprises specifying a region of the body part and limiting the additional imaging data to the specified region.

18. The method of claim 9, wherein prescribing collection of additional imaging data comprises prescribing a different imaging technique or prescribing collection at an increased resolution.

19. The method of claim 9, further comprising repeating the steps of: receiving imaging data, classifying by machine learning the imaging data, and suggesting collection of additional imaging data.

20. The method of claim 15, further comprising:
processing by the CNN each image of the batch of images according to a tensor having at least a batch dimension, and at least two spatial dimensions; and
reshaping the tensor to a variable batch dimension.

* * * * *